(12) United States Patent
Okeley et al.

(10) Patent No.: US 11,891,644 B2
(45) Date of Patent: Feb. 6, 2024

(54) T CELLS WITH REDUCED SURFACE FUCOSYLATION AND METHODS OF MAKING AND USING THE SAME

(71) Applicant: Seagen Inc., Bothell, WA (US)

(72) Inventors: Nicole Okeley, Bothell, WA (US); Jessica Field, Bothell, WA (US); Shyra Gardai, Bothell, WA (US); Ryan Heiser, Lake Stevens, WA (US)

(73) Assignee: Seagen Inc., Bothell, WA (US)

( * ) Notice: Subject to any disclaimer, the term of this patent is extended or adjusted under 35 U.S.C. 154(b) by 758 days.

(21) Appl. No.: 16/616,928

(22) PCT Filed: Jun. 5, 2018

(86) PCT No.: PCT/US2018/036067
§ 371 (c)(1),
(2) Date: Nov. 25, 2019

(87) PCT Pub. No.: WO2018/226701
PCT Pub. Date: Dec. 13, 2018

(65) Prior Publication Data
US 2020/0149082 A1 May 14, 2020

Related U.S. Application Data

(60) Provisional application No. 62/516,536, filed on Jun. 7, 2017.

(51) Int. Cl.
| | | |
|---|---|---|
| *C12P 21/00* | (2006.01) | |
| *A61P 35/02* | (2006.01) | |
| *A61K 31/7024* | (2006.01) | |
| *A61K 35/17* | (2015.01) | |
| *C12N 5/0783* | (2010.01) | |
| *A61K 31/70* | (2006.01) | |

(52) U.S. Cl.
CPC ............ *C12P 21/005* (2013.01); *A61K 31/70* (2013.01); *A61K 31/7024* (2013.01); *A61K 35/17* (2013.01); *A61P 35/02* (2018.01); *C12N 5/0636* (2013.01); *C12N 2500/34* (2013.01)

(58) Field of Classification Search
CPC ........ C12P 21/005; A61P 35/02; A61K 31/70; A61K 31/7024; A61K 35/17; C12N 5/0636; C12N 2500/34
USPC ........................................................ 435/375
See application file for complete search history.

(56) References Cited

U.S. PATENT DOCUMENTS

| | | |
|---|---|---|
| 4,683,195 A | 7/1987 | Mullis et al. |
| 2016/0158359 A1 | 6/2016 | Gilbert |

FOREIGN PATENT DOCUMENTS

| | | | |
|---|---|---|---|
| WO | WO 2012/019165 A2 * | 2/2012 | |
| WO | WO2012019165 A2 | 2/2012 | |
| WO | 2012177925 A1 | 12/2012 | |
| WO | WO2012019165 A3 | 8/2013 | |
| WO | WO2015120096 A2 | 8/2015 | |
| WO | WO2015164675 A1 | 10/2015 | |
| WO | WO2015120096 A3 | 11/2015 | |
| WO | WO2016011210 A2 | 1/2016 | |
| WO | WO2016011210 A3 | 3/2016 | |
| WO | WO2016040441 A1 | 3/2016 | |
| WO | WO2017070395 A1 | 4/2017 | |
| WO | WO2017096274 A1 | 6/2017 | |

OTHER PUBLICATIONS

Fujii et al. Core Fucosylation on T Cells, Required for Activation of T-Cell Receptor Signaling and Induction of Colitis in Mice, Is Increased in Patients With Inflammatory Bowel Disease. Gastroenterology 2016;150:1620-1632. (Year: 2016).*
Field et al. Abstract 4005: Understanding the mechanism of 2FF-induced immune modulation. Cancer Res (2016) 76 (14_Supplement): 4005. https://doi.org/10.1158/1538-7445.AM2016-4005 (Jul. 15, 2016) (Year: 2016).*
Alley, S.C. et al. (Apr. 1, 2017). "Abstract DDT02-02: SGN-2FF: A Novel Small Molecule Inhibitor of Fucosylation With Preclinical Antitumor Activity Through Multiple Immune Mechanism," Proceedings: AACR Annual Meeting, 2 pages.
Field, J.J. et al. (Jul. 15, 2016). "Abstract 4005: Understanding the Mechanism of 2FF-Inducted Immune Modulation," Cancer Research p. 4005, 1 page.
Freshney, R.I. (2005). Culture of Animal Cells: A Manual of Basic Technique, 5th Edition, John Wiley & Sons, Inc. pp. 115-128. TOC.
International Preliminary Report on Patentabilty, dated Dec. 10, 2019, for PCT Application No. PCT/US2018/036067, filed Jun. 5, 2018, 7 pages.
International Search Report and Written Opinion, dated Aug. 20, 2018, for PCT Application No. PCT/US2018/036067, filed Jun. 5, 2018, 10 pages.
Okada, M. et al. (Aug. 1, 2017). "Blockage of Core Fucosylation Reduces Cell-Surface Expression of PD-1 and Promotes Anti-Tumor Immune Responses of T Cells," Cell Reports 20(5):1017-1028.
Perica, K. et al. (Jan. 29, 2015). "Adoptive T Cell Immunotherapy for Cancer," Rambam Maimonides Medical Journal 6(1):e004, 9 pages.
Roig, M.G. (1985). Immobilized Cells and Enzymes—A Practical Approach Abstract, 1 page.
Field, J.J. et al. (2016). "The Fucosylation Inhibitor 2-FlIIuorofucose Exhibits Anti-Tumor Activity and Modulates Immuned Cell Activity Both in vitro and in vivo," Journal for Immunotherapy of Cancer 4(Suppl. 1):73, 2 pages.
Zhong, R.K. et al. (2006). "CTLA-4 Blockade by a Human Mab Enhances the Capacity of AML-Derived DC to Induce T-Cell Responses Against AML Cells in an Autologous Culture System," Cytotherapy 8(1):3-12.

* cited by examiner

*Primary Examiner* — Yih-Horng Shiao
(74) *Attorney, Agent, or Firm* — MORRISON & FOERSTER LLP

(57) ABSTRACT

Methods of producing T cells having reduced surface fucosylation and use thereof in adoptive cell therapy, in particular, in cancer treatment are provided.

8 Claims, 6 Drawing Sheets

T CELLS WITH REDUCED SURFACE FUCOSYLATION AND METHODS OF MAKING AND USING THE SAME

CROSS REFERENCE TO RELATED APPLICATIONS

This application is a national stage application under 35 U.S.C. § 371 of International Application No. PCT/US2018/036067, filed internationally on Jun. 5, 2018, which claims priority benefit under 35 U.S.C. § 119(e) of U.S. Provisional Application No. 62/516,536 filed Jun. 7, 2017, which are incorporated herein by reference in their entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

There have been generally three approaches adopted in cancer treatment: surgery, chemotherapy, and radiotherapy. Additionally, immunotherapy has emerged as a relatively new and still experimental approach that can be potentially applied alone or in combination with any existing approaches in cancer treatment. One of treatment modalities within cancer immunotherapy is adoptive cell therapy using tumor-specific T cells. In order to make the adoptive cell therapy, improved strategies are needed, for example, to provide T cells specific to a target disease, e.g. a specific type of cancer to be treated in a patient while avoiding off-target effects on non-pathogenic tissues.

BRIEF SUMMARY OF THE INVENTION

In one aspect, methods for producing T cells having reduced surface fucosylation are provided. In some aspects, the methods include culturing T cells in the presence of a fucose analog in a cell culture medium; wherein the fucose analog has formula (I) or (II):

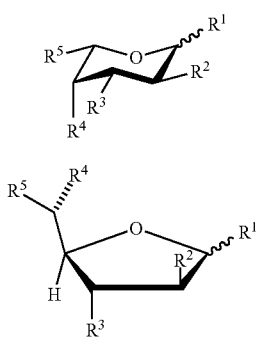

or a pharmaceutically acceptable salt or solvate form thereof, wherein each of formula (I) or (II) can be the alpha or beta anomer or the corresponding aldose form;
$R^2$ is halogen; each of $R^1$, $R^3$, and $R^4$ is independently —OH or a hydrolyzable ester group; and $R^5$ is —$CH_3$, or
each of $R^1$, $R^2$, $R^3$, and $R^4$ is independently —OH or a hydrolyzable ester group; and $R^5$ is —C≡CH; and
wherein the T cells having reduced surface fucosylation relative to T cells cultured in the absence of the fucose analog.

In another aspect, methods for producing T cells having reduced surface fucosylation are provided. In some aspects, the methods include providing a fucose analog to an animal and obtaining T cells having reduced surface fucosylation from the animal; wherein the fucose analog has formula (I) or (II):

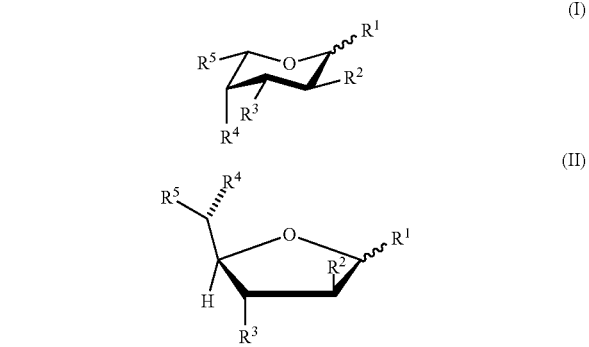

or a pharmaceutically acceptable salt or solvate form thereof, wherein each of formula (I) or (II) can be the alpha or beta anomer or the corresponding aldose form;
$R^2$ is halogen; each of $R^1$, $R^3$, and $R^4$ is independently —OH or a hydrolyzable ester group; and $R^5$ is —$CH_3$, or
each of $R^1$, $R^2$, $R^3$, and $R^4$ is independently —OH or a hydrolyzable ester group; and $R^5$ is —C≡CH; and
wherein the T cells obtained from the animal have reduced surface fucosylation relative to T cells present in or obtained from a control animal that was not provided with said fucose analog.

In still another aspect, methods for providing an adoptive cell therapy to a subject are provided. In some aspects, the methods include administering a mixture having T cells with reduced surface fucosylation to the subject in need of the cell therapy.

In still another aspect, methods for treating a cancer are provided. In some aspects, the methods include administering a mixture having T cells with reduced surface fucosylation to the subject in need of the cancer treatment.

In still another aspect, methods for treating a cancer are provided. In some aspects, the method include administering a mixture having T cells with reduced surface fucosylation to the subject in need of the cancer treatment, wherein the T cells with reduced surface fucosylation are produced according to any methods for producing such T cells.

These and other aspects of the disclosures provided herein can be more fully understood by reference to the following detailed description, non-limiting examples of specific embodiments, and the appended figures.

BRIEF DESCRIPTION OF THE DRAWINGS

FIG. 5A shows the graph demonstrating tumor progression via caliper measurements and FIG. 5B shows the graph demonstrating tumor progression via survival.

DETAILED DESCRIPTION OF THE INVENTION

Figure 1:
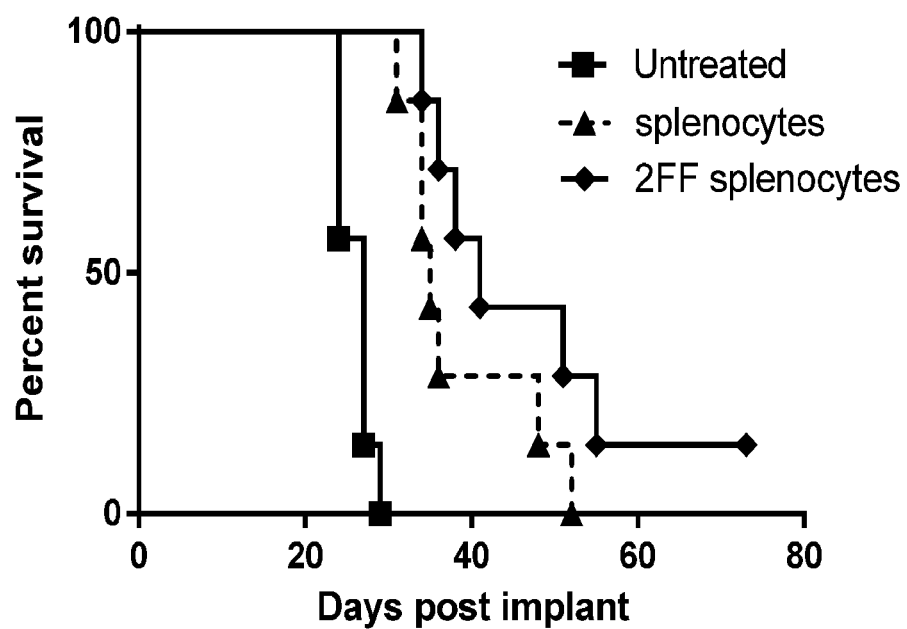
FIG. 1 shows a graph demonstrating in vivo effects of the adoptive transfer of splenocytes from KLH-A20 Id Fab vaccinated donor mice that were either treated or not with 2FF on the growth of IV implanted A20 mouse lymphoma cells in naïve BALB/c mice.

While various embodiments and aspects of the disclosures herewith are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein can be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The practice of the present disclosure will employ, unless otherwise indicated, conventional techniques of tissue culture, immunology, molecular biology and cell biology, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (2002) Cold Spring Harbor Laboratory Press; Sohail (2004) Gene Silencing by RNA Interference: Technology and Application (CRC Press).

I. DEFINITIONS

As used herein and in the appended claims, the singular forms "a", "an", and "the" include plural referents unless the context clearly dictates otherwise. Thus, for example, reference to "a fucose analog" includes one or more fucose analogs. When a plurality of fucose analogs are meant, each of the plurality of fucose analogs can be identical or different.

The term "isolate", "isolating" or "isolated" is intended to mean that a component (e.g. a compound or cell) is separated from all or some of the components that accompany it in nature or in a lab mixture.

The term "enrich", "enriching" or "enriched" is intended to mean that a mixture having a component (e.g. a compound or cell) is processed to increase a concentration of the component compared to prior to the process. For example, enriching T cells from a mixture of cells including T cells and other types of cells means that the mixture of cells is processed, e.g. centrifugation, such that a concentration or number of T cells per unit volume before the enrichment, e.g. $10^5$ T cells/ml is increased to be more than $10^5$ T cells/ml after the enrichment process.

The term "culture" or "cell culture" means the maintenance and/or growth of cells in an artificial, in vitro environment. A "cell culture system" is used herein to refer to culture conditions in which a population of cells can be grown. "Culture medium" is used herein to refer to a nutrient solution for the culturing, growth, or proliferation of cells.

By "composition" used herein refers to any compounds (including any chemical compounds) and cells, which can be living or killed. For example, in the context of producing T cells with reduced surface fucosylation, the composition can contain a fucose analog that is provided to the cultured cells. In another example, in the context of providing an adoptive cell therapy or treating a cancer, the composition can contain a group of cells, e.g. T cells having reduced surface fucosylation. A composition used in any context can have one or more components.

The terms "T lymphocyte" or "T cell" refer to a type of lymphocyte that plays a role in cell-mediated immunity. The types of T cell include, but not limited to, effector T cells, helper T cells, cytotoxic killer T cells, memory T cells, regulatory T cells, natural killer T cell, mucosal-associated invariant T cells, alpha beta T cells, and gamma delta T cells. Also, T cells can be further subtyped depending on the presence or level of one or more particular markers thereon.

The terms "individual" or "subject" as used herein refers to humans, mammals and other animals in the present disclosure. In some cases, the subject being a human can be a patient.

By "treatment" in the context of disease or condition is meant that at least an amelioration of the symptoms associated with the condition afflicting an individual is achieved, where amelioration is used in a broad sense to refer to at least a reduction in the magnitude of a parameter, e.g. symptom, associated with the condition (e.g., cancer) being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells; and/or (iii) relief, that is, causing the regression of clinical symptoms.

"Administration," "administering" and the like refer both to direct administration, which can be administration to cells in vitro, administration to cells in vivo, administration to a subject by a medical professional and/or to indirect administration, which can be the act of prescribing a composition of the invention. When used herein in reference to a cell, refers to introducing a composition to the cell. Typically, an effective amount is administered, which amount can be determined by one of skill in the art. For example, when one or more fucose analogs are administered to cells cultured in a culture medium, the effective amount of the fucose analog(s) is defined as an amount that is sufficient to produce a desired effect, e.g. production of T cells having reduced surface fucosylation. Any method of administration can be used. Compounds (e.g., one or more fucose analogs) can be administered to the cells by, for example, addition of the compounds to the cell culture media or administration (e.g. feeding) in vivo. Administration to a subject can be achieved by, for example, feeding, intravascular injection, direct intratumoral delivery, and the like.

Administering can mean oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the composition individually or in combination (more than one composition). Thus, the preparations can also be combined, when desired, with other active substances (e.g. to reduce metabolic degradation).

The term "cancer" as used herein refers to a general term encompassing primary cancer and metastatic cancer. By "primary cancer" is meant a group of tumor cells, which have acquired at least one characteristic feature of cancer cells, however have not yet invaded the neighboring tissues and hold together in a tumor localized at the place of primary origin. By "metastatic cancer" is meant a group of tumor cells, which originate from the cells of a primary cancer, which have invaded the tissue surrounding said primary cancer, disseminated through the body, adhered at a new distant place and grown to a new tumor. The examples of primary and metastatic cancers of the present invention include, but is not limited by carcinoma of the breast, esophageal cancer, colorectal, pancreas, stomach, (gastrointestinal stromal tissue) GIST, hepatocellular, liver, lung, small cell lung, ovarian, uterine, cervix, bladder, renal, colon, small intestine, large intestine, gastric cancer, lymphoma, prostate, testis, thyroid carcinoma, malignant melanoma, uveal melanoma, multiple myeloma, mesothelioma, osteosarcoma, chondrosarcoma, myosarcoma, glioblastoma, sarcoma, glioma, or other brain tumors, head/neck other gastrointestinal and germ cell tumors, haematologic malignancies, leukemia, lymphoma, e.g., chronic lymphocytic leukemia (CLL), acute lymphoid leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of skin (including melanoma), bone cancers, epithelial cancers, renal cell carcinoma, pancreatic adenocarcinoma, Hodgkin lymphoma, glioblastoma, neuroblastoma, Ewing sarcoma, medulloblastoma, synovial sarcoma, and/or mesothelioma.

A "cancer cell" as used herein refers to a cell exhibiting a neoplastic cellular phenotype, which can be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" can be used interchangeably herein with "tumor cell" or "cancerous cell", and encompasses cancer cells of a solid tumor, a semi-solid tumor, a primary tumor, a metastatic tumor, and the like.

An "anti-tumor effect" or "anti-cancer effect" as used herein, refers to a biological effect that can present as a decrease in tumor volume, an inhibition of tumor growth, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival" which can be abbreviated as PFS, as used herein refers to the time from the treatment date to the date of disease progression per the revised International Working Group (IWG) Response Criteria for Malignant Lymphoma or death from any cause.

The term "overall survival" which can be abbreviated as OS, is defined as the time from the date of treatment to the date of death.

The term "adoptive cell therapy" or "adoptive cell transfer" as used herein refers to provision, e.g. administration or transplantation of cells for therapy into a subject that is in need of the therapy. The cells for therapy can originate from the same subject or from another subject including a human and non-human animal. Cells for adoptive cell therapy or adoptive cell transfer can include T cells.

According to the methods provided herein, a subject can be administered with an adoptive cell therapy. Some examples on the methods and procedures related to adoptive cell therapy can be found from, e.g. WO2015120096, WO2015164675, WO2016011210, WO2016040441, WO2017070395, and US20160158359, disclosures of which are expressly incorporated by reference in their entirety. The adoptive cell therapy can provide a mixture of cells including T cells, especially T cells with reduced surface fucosylation, to the subject. The amount of T cells administered to the subject that can produce a desired physiologic response (e.g., inhibition or reduction of tumor growth) is defined as an effective amount. The terms effective amount and effective dosage are used interchangeably. For instance, for eliciting a favorable response in a subject to treat a disease (e.g., cancer), the effective amount is the amount which reduces, eliminates or diminishes the symptoms associated with the disorder, e.g., so as to provide for control of cancer metastasis, to eliminate cancer cells, and/or the like. Effective amounts and schedules for administering the T cells can be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. For example, for the given parameter, an effective amount will show an increase or decrease of at least 5%, 10%, 15%, 20%, 25%, 40%, 50%, 60%, 75%, 80%, 90%, or at least 100% as compared to a pre-treatment. Efficacy can also be expressed as "-fold" increase or decrease. For example, a therapeutically effective amount can have at least a 1.2-fold, 1.5-fold, 2-fold, 5-fold, or more effect over a control or pre-treatment. The exact dose and formulation will depend on the purpose of the therapy and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

The term "reduced surface fucosylation" as used herein refers to the inhibition of fucose attached to the surface glycoproteins on cells, e.g., T cells. Such "inhibition of fucose" is distinct from competitive incorporation by a fucose analog wherein the fucose analog replaces fucose on the surface glycoproteins.

A "control" or "normal" sample, e.g. control cells or normal cells, refers to a sample that serves as a reference, usually a known reference, for comparison to a test sample. For example, a test sample can be modified T cells, in particular, T cells having reduced surface fucosylation. Such T cells can be produced by the methods disclosed herein, e.g. via culturing T cells in the presence of a fucose analog or obtaining T cells from an animal that was administered with a fucose analog. These modified T cells can be compared to control or normal T cells that were cultured in the absences of a fucose analog or obtained from an animal that was not administered with a fucose analog so as to confirm the reduction. A control value can also be obtained from the same individual, e.g., from an earlier-obtained sample, prior to exposure or administration of a fucose analog.

The term "pharmaceutically acceptable excipient" as used herein refers to any suitable substance which provides a pharmaceutically acceptable compound for administration of a compound(s) of interest to a subject. "Pharmaceutically acceptable excipient" can encompass substances referred to as pharmaceutically acceptable diluents, pharmaceutically acceptable additives and pharmaceutically acceptable carriers. The term "carrier" or "pharmaceutically acceptable carrier" refers to a diluent, adjuvant or excipient, with which a fucose analog is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the fucose analogs or compositions and pharmaceutically acceptable carriers are sterile. Water is a preferred carrier when the fucose analogs are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

As used herein, "hydrolyzable ester groups" refers to any conventional ester, which can be hydrolyzed in vivo to yield the hydroxy group. Exemplary hydrolyzable ester groups include —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O) heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), —OC(O)C$_2$-C$_{10}$ alkynylene(heterocycle), —OC(O)CH$_2$O(CH$_2$CH$_2$O)$_n$CH$_3$, and —OC(O)CH$_2$CH$_2$O(CH$_2$CH$_2$O)$_n$CH$_3$, wherein each n is an integer independently selected from 0-5.

As used herein, "alkynyl fucose peracetate" refers to any or all forms of alkynyl fucose (5-ethynylarabinose) with acetate groups on positions $R^{1-4}$ (see formula I and II, infra), including 6-ethynyl-tetrahydro-2H-pyran-2,3,4,5-tetrayl tetraacetate, including the (2S,3S,4R,5R,6S) and (2R,3S,4R,5R,6S) isomers, and 5-((S)-1-hydroxyprop-2-ynyl)-tetrahydrofuran-2,3,4-triyl tetraacetate, including the (2S,3S,4R,5R) and (2R,3S,4R,5R) isomers, and the aldose form, unless otherwise indicated by context. The terms "alkynyl fucose triacetate", "alkynyl fucose diacetate" and "alkynyl fucose monoacetate" refer to the indicated tri-, di- and mono-acetate forms of alkynyl fucose, respectively.

Unless otherwise indicated by context, the term "alkyl" refers to an unsubstituted saturated straight or branched hydrocarbon having from 1 to 20 carbon atoms (and all combinations and subcombinations of ranges and specific numbers of carbon atoms therein), unless otherwise specified. An alkyl group of 1 to 3, 1 to 8 or 1 to 10 carbon atoms is preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from —H, —$C_1$-$C_8$ alkyl, —$C_2$-$C_8$ alkenyl, —$C_2$-$C_8$ alkynyl, or aryl.

Unless otherwise indicated by context, the terms "alkenyl" and "alkynyl" refer to unsubstituted or optionally substituted (were indicated) straight and branched carbon chains having from 2 to 20 carbon atoms (and all combinations and subcombinations of ranges and specific numbers of carbon atoms therein), with from 2 to 3, 2 to 4, 2 to 8 or 2 to 10 carbon atoms being preferred. An alkenyl chain has at least one double bond in the chain and an alkynyl chain has at least one triple bond in the chain. Examples of alkenyl groups include, but are not limited to, ethylene or vinyl, allyl, -1 butenyl, -2 butenyl, -isobutylenyl, -1 pentenyl, -2 pentenyl, 3-methyl-1-butenyl, -2 methyl 2 butenyl, and -2,3 dimethyl 2 butenyl. Examples of alkynyl groups include, but are not limited to, acetylenic, propargyl, acetylenyl, propynyl, -1 butynyl, -2 butynyl, -1 pentynyl, -2 pentynyl, and -3 methyl 1 butynyl.

Alkenyl and alkynyl groups, whether alone or as part of another group, when substituted can be substituted with one or more groups, preferably 1 to 3 groups (and any additional substituents selected from halogen), including but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$—C alkenyl, —$C_2$-$C_8$ alkynyl, or aryl.

Unless otherwise indicated by context, the term "alkylene" refers to an unsubstituted saturated branched or straight chain hydrocarbon radical having from 1 to 20 carbon atoms (and all combinations and subcombinations of ranges and specific numbers of carbon atoms therein), with from 1 to 8 or 1 to 10 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like.

Alkylene groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or -aryl.

"Alkenylene" refers to an unsaturated, branched or straight chain or cyclic hydrocarbon radical of an alkenyl group (as described above), and having two monovalent radical centers derived by the removal of two hydrogen atoms from the same or two different carbon atoms of a parent alkene. An "alkenylene" group can be unsubstituted or optionally substituted (were indicated), as described above for alkenyl groups. In some embodiments, an "alkenylene" group is not substituted.

"Alkynylene" refers to an unsaturated, branched or straight chain or cyclic hydrocarbon radical of an alkynyl group (as described above), and having two monovalent radical centers derived by the removal of two hydrogen atoms from the same or two different carbon atoms of a parent alkyne. An "alkynylene" group can be unsubstituted or optionally substituted (were indicated), as described above for alkynyl groups. In some embodiments, an "alkynylene" group is not substituted.

Unless otherwise indicated by context, the term "aryl" refers to a substituted or unsubstituted monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to: halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, —$NO_2$, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl.

Unless otherwise indicated by context, the term "heterocycle" refers to a substituted or unsubstituted monocyclic ring system having from 3 to 7, or 3 to 10, ring atoms (also referred to as ring members) wherein at least one ring atom is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960). Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, fucosyl, azirdinyl, azetidinyl, oxiranyl, oxetanyl, and tetrahydrofuranyl.

A heterocycle group, whether alone or as part of another group, when substituted can be substituted with one or more groups, preferably 1 to 2 groups, including but not limited to: —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3R^1$, —S(O)$_2$R', —S(O)R', —OH, —$NH_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or -aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; or position 2, 3, or 4 of an azetidine. Exemplary carbon bonded heterocycles can include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazolidine, 2-pyrazoline, 3-pyrazoline, piperidine, piperazine, indole, indoline, or 1H-indazole; position 2 of a isoindole, or isoindoline; and position 4 of a morpholine. Still more typically, nitrogen bonded heterocycles include 1-aziridyl, 1-azetidyl, 1-pyrrolyl, 1-imidazolyl, 1-pyrazolyl, and 1-piperidinyl.

Unless otherwise noted, the term "carbocycle," refers to a substituted or unsubstituted, saturated or unsaturated non-aromatic monocyclic ring system having from 3 to 6 ring atoms (and all combinations and subcombinations of ranges and specific numbers of carbon atoms therein) wherein all of the ring atoms are carbon atoms.

Carbocycle groups, whether alone or as part of another group, when substituted can be substituted with, for example, one or more groups, preferably 1 or 2 groups (and any additional substituents selected from halogen), including, but not limited to: halogen, C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or aryl.

Examples of monocyclic carbocylic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, cyclooctyl, -1,3-cyclohexadienyl, -1,4-cyclohexadienyl, -1,3-cycloheptadienyl, -1,3,5-cycloheptatrienyl, and -cyclooctadienyl.

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—(C$_1$-C$_{10}$ alkylene)aryl" or "—C$_1$-C$_{10}$ alkylene(aryl)" refers to a C$_1$-C$_{10}$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group can have one or more substituents, preferably from one to five substituents, more preferably from one to three substituents, most preferably from one to two substituents, independently selected from the list of substituents. The group can, however, generally have any number of substituents selected from halogen.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are active and chemically stable and that can be readily synthesized by techniques known in the art as well as those methods set forth herein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which the fucose analog is administered.

The fucose analogs are typically substantially pure from undesired contaminant. This means that the analog is typically at least about 50% w/w (weight/weight) purity, as well as being substantially free from interfering proteins and other contaminants. Sometimes the agents are at least about 80% w/w and, more preferably at least 90% or about 95% w/w purity. Using conventional purification techniques, homogeneous product of at least 99% w/w can be obtained.

II. FUCOSE ANALOGS

In any of the various embodiments herein, the fucose analog can have the following formula (I) or (II):

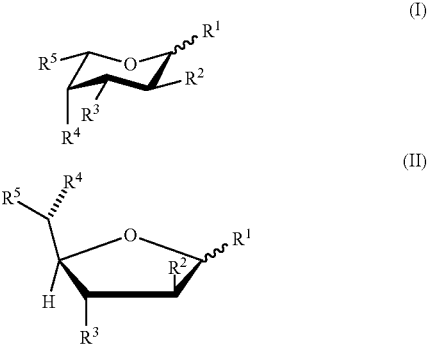

or a pharmaceutically acceptable salt or solvate form thereof, wherein each of formula (I) or (II) can be the alpha or beta anomer or the corresponding aldose form;

wherein $R^2$ is halogen; each of $R^1$, $R^3$, and $R^4$ is independently —OH or a hydrolyzable ester group; and $R^5$ is —CH$_3$, or wherein each of $R^1$, $R^2$, $R^3$, and $R^4$ is independently —OH or a hydrolyzable ester group; and $R^5$ is alkynyl.

In some embodiments, $R^2$ is —F.

In some embodiments, $R^5$ is —C≡CH.

In some embodiments, the fucose analog has formula (I) or (II), wherein $R^2$ is halogen; each of $R^1$, $R^3$, and $R^4$ is independently —OH or a hydrolyzable ester group; and $R^5$ is —$CH_3$, or wherein each of $R^1$, $R^2$, $R^3$, and $R^4$ is independently —OH or a hydrolyzable ester group; and $R^5$ is —C≡CH.

In some embodiments, the fucose analog has formula (I) or (II), wherein $R^2$ is —F; each of $R^1$, $R^3$, and $R^4$ is independently —OH or a hydrolyzable ester group; and $R^5$ is —$CH_3$, or wherein each of $R^1$, $R^2$, $R^3$, and $R^4$ is independently —OH or a hydrolyzable ester group; and $R^5$ is —C≡CH.

In some selected embodiments of formula (I) or (II), $R^2$ is halogen; each of $R^1$, $R^3$, and $R^4$ is independently —OH or a hydrolyzable ester group; and $R^5$ is —$CH_3$. In some selected embodiments of formula (I) or (II), $R^2$ is —F; each of $R^1$, $R^3$, and $R^4$ is independently —OH or a hydrolyzable ester group; and $R^5$ is —$CH_3$.

In some selected embodiments of formula (I) or (II), each of $R^1$, $R^2$, $R^3$, and $R^4$ is independently —OH or a hydrolyzable ester group; and $R^5$ is —C≡CH.

In some embodiments, the hydrolyzable ester group is —OC(O)$C_1$-$C_{10}$ alkyl. In some selected embodiments, the hydrolyzable ester group is —OC(O)$CH_3$.

In some selected embodiments of formula (I) or (II) wherein $R^2$ is —F, each of $R^1$, $R^3$ and $R^4$ is independently selected from the group consisting of —OH and —OC(O)$C_1$-$C_{10}$ alkyl. In some selected embodiments of formulae (I) or (II) wherein $R^2$ is —F, each of $R^1$, $R^3$ and $R^4$ is independently selected from the group consisting of —OH and —OC(O)$CH_3$. In one specific embodiment of formula (I) or (II), $R^2$ is —F and each of $R^1$, $R^3$ and $R^4$ is —OH.

In some selected embodiments of formula (I) or (II) wherein $R^5$ is —CH, each of $R^1$, $R^2$, $R^3$ and $R^4$ is independently selected from the group consisting of —OH and —OC(O)$C_1$-$C_{10}$ alkyl. In some selected embodiments of formula (I) or (II) wherein $R^5$ is —C≡CH, each of $R^1$, $R^2$, $R^3$ and $R^4$ is independently selected from the group consisting of —OH and —OC(O)$CH_3$. In one specific embodiment of formula (I) or (II), $R^5$ is —C≡CH and each of $R^1$, $R^2$, $R^3$ and $R^4$ is —OH. In another specific embodiment of formula (I) or (II), $R^5$ is —C≡CH and each of $R^1$, $R^2$, $R^3$ and $R^4$ is —OAc.

In some selected embodiments, the fucose analog has the formula:

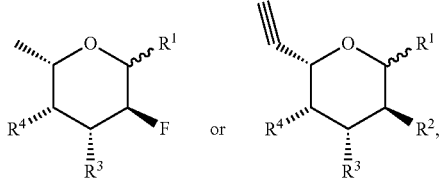

or an aldose form thereof, wherein each of $R^1$, $R^2$, $R^3$, and $R^4$ is as defined and described herein.

In some selected embodiments, the fucose analog is 2-deoxy-2-fluoro-L-fucose.

In some selected embodiments, the fucose analog is alkynyl fucose peracetate. Alkynyl fucose peracetate can be alkynyl fucose tetraacetate, alkynyl fucose triacetate, alkynyl fucose diacetate, alkynyl fucose monoacetate, or combinations thereof. In one exemplified embodiment, the fucose analog is (3S,4R,5R,6S)-6-ethynyltetrahydro-2H-pyran-2,3,4,5-tetrayl tetraacetate or 5-((S)-1-hydroxyprop-2-yn-1-yl)tetrahydrofuran-2,3,4-triyltriacetate.

In any of the various embodiments, the endocylic ring oxygen of the fucose analog of formulae (I) and (II) can be replaced by sulfur.

Also provided herein are the pharmaceutically acceptable salt and solvate forms of the compounds of formulae I and II. Accordingly, in any of the various embodiments provided herein, the pharmaceutically acceptable salt or solvate forms of the disclosed compounds can be used. Solvates typically do not significantly alter the physiological activity of the compounds and as such can function as pharmacological equivalents. One type of solvate is a hydrate.

In some aspects, the fucose analog is soluble in formulation buffer (e.g. aqueous formulation buffer) at a concentration of at least 10 mM. In some embodiments, the fucose analog is soluble in formulation buffer at a concentration of at least 100 mM. In some aspects, the fucose analog is soluble in formulation buffer (e.g. aqueous formulation buffer) at a concentration of at least 100 μg/ml, at least 1 mg/ml, at least 50 mg/ml, at least about 100 mg/ml, at least about 200 mg/ml, or at least about 300 mg/ml.

III. METHOD OF PRODUCING T CELLS WITH REDUCED SURFACE FUCOSYLATION

In some aspects, methods of producing T cells having reduced surface fucosylation are provided herein.

II-1. In Vitro or Ex Vivo Production Methods

In some aspects, in vitro or ex vivo methods of producing T cells having reduced surface fucosylation are provided. The methods can include culturing T cells in the presence of a fucose analog disclosed herein in a cell culture medium and collecting the T cells having reduced surface fucosylation. The T cells produced by the method can have reduced surface fucosylation as compared to T cells cultured in the absence of a fucose analog. Such T cells produced by the methods disclosed herein can be used for therapeutic purposes such as an adoptive cell therapy or cancer treatment. Therefore, at least in some embodiments, the T cells having reduced surface fucosylation are referred to as "therapeutic T cells".

In some embodiments, the fucose analog used in the methods can be formula (I) or (II):

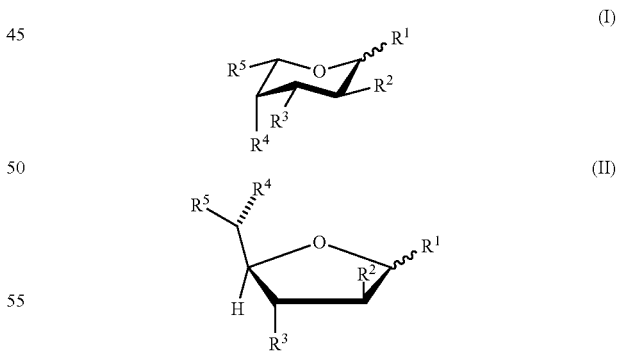

or a pharmaceutically acceptable salt or solvate form thereof, wherein each of formula (I) or (II) can be the alpha or beta anomer or the corresponding aldose form;

wherein $R^2$ is halogen; each of $R^1$, $R^3$, and $R^4$ is independently —OH or a hydrolyzable ester group; and $R^5$ is —$CH_3$, or wherein each of $R^1$, $R^2$, $R^3$, and $R^4$ is independently —OH or a hydrolyzable ester group; and $R^5$ is alkynyl.

In some embodiments, $R^2$ is —F.

In some embodiments, $R^5$ is —C≡CH.

In some embodiments, the fucose analog used in the methods has formula (I) or (II), wherein $R^2$ is halogen; each of $R^1$, $R^3$, and $R^4$ is independently —OH or a hydrolyzable ester group; and $R^5$ is —CH$_3$, or wherein each of $R^1$, $R^2$, $R^3$, and $R^4$ is independently —OH or a hydrolyzable ester group; and $R^5$ is —C≡CH.

In some embodiments, the fucose analog used in the methods has formula (I) or (II), wherein $R^2$ is —F; each of $R^1$, $R^3$, and $R^4$ is independently —OH or a hydrolyzable ester group; and $R^5$ is —CH$_3$, or wherein each of $R^1$, $R^2$, $R^3$, and $R^4$ is independently —OH or a hydrolyzable ester group; and $R^5$ is —C≡CH.

In some selected embodiments of formula (I) or (II), $R^2$ is halogen; each of $R^1$, $R^3$, and $R^4$ is independently —OH or a hydrolyzable ester group; and $R^5$ is —CH$_3$. In some selected embodiments of formula (I) or (II), $R^2$ is —F; each of $R^1$, $R^3$, and $R^4$ is independently —OH or a hydrolyzable ester group; and $R^5$ is —CH$_3$.

In some selected embodiments of formula (I) or (II), each of $R^1$, $R^2$, $R^3$, and $R^4$ is independently selected from —OH, or a hydrolyzable ester group; and $R^5$ is —C≡CH.

In some embodiments, the hydrolyzable ester group is —OC(O)C$_1$-C$_{10}$ alkyl. In some selected embodiments, the hydrolyzable ester group is —OC(O)CH$_3$.

In some selected embodiments of formula (I) or (II) wherein $R^2$ is —F, each of $R^1$, $R^3$ and $R^4$ is independently selected from the group consisting of —OH and —OC(O)C$_1$-C$_{10}$ alkyl. In some selected embodiments of formula (I) or (II) wherein $R^2$ is —F, each of $R^1$, $R^3$ and $R^4$ is independently selected from the group consisting of —OH and —OC(O)CH$_3$. In one specific embodiment of formula (I) or (II), $R^2$ is —F and each of $R^1$, $R^3$ and $R^4$ is —OH.

In some selected embodiments of formula (I) or (II) wherein $R^5$ is —CH, each of $R^1$, $R^2$, $R^3$ and $R^4$ is independently selected from the group consisting of —OH and —OC(O)C$_1$-C$_{10}$ alkyl. In some selected embodiments of formula (I) or (II) wherein $R^5$ is —C≡CH, each of $R^1$, $R^2$, $R^3$ and $R^4$ is independently selected from the group consisting of —OH and —OC(O)CH$_3$. In one specific embodiment of formula (I) or (II), $R^5$ is —C≡CH and each of $R^1$, $R^2$, $R^3$ and $R^4$ is —OH. In another specific embodiment of formula (I) or (II), $R^5$ is —C≡CH and each of $R^1$, $R^2$, $R^3$ and $R^4$ is —OAc.

In some selected embodiments, the fucose analog used in the methods has the formula:

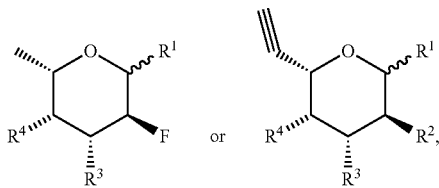

or an aldose form thereof, wherein each of $R^1$, $R^2$, $R^3$, and $R^4$ is as defined and described herein.

In some selected embodiments, the fucose analog is 2-deoxy-2-fluoro-L-fucose.

In some selected embodiments, the fucose analog is alkynyl fucose peracetate. Alkynyl fucose peracetate can be alkynyl fucose tetraacetate, alkynyl fucose triacetate, alkynyl fucose diacetate, alkynyl fucose monoacetate, or combinations thereof. In one exemplified embodiment, the fucose analog is (3S,4R,5R,6S)-6-ethynyltetrahydro-2H-pyran-2,3,4,5-tetrayl tetraacetate or 5-((S)-1-hydroxyprop-2-yn-1-yl)tetrahydrofuran-2,3,4-triyl triacetate.

In any of the various embodiments, the endocylic ring oxygen of the fucose analog of formulae (I) and (II) can be replaced by sulfur.

In some embodiments, the methods disclosed herein can include a step of culturing T cells in the presence of a fucose analog in a cull culture medium. In some embodiments, there are other types of cells, e.g. red blood cells present in the culture media. The T cells to be cultured can be obtained from a subject (e.g. a human or non-human animal). Alternatively, the T cells to be cultured can be from a previously cultured and/or stored population of cells.

In some embodiments, the methods disclosed herein produce T cells having reduced surface fucosylation which can be used in an adoptive cell therapy for a subject in need of such therapy. In embodiments where the T cells and cell populations are isolated from a sample, such as a biological sample, e.g., one obtained from or derived from a subject, the subject can be a patient who is in need of a cell therapy or to which cell therapy will be administered, i.e. an autologous source. Alternatively, the T cells and cell populations can be isolated from a donor that is not a patient who is in need of an adoptive cell therapy, i.e. an allogenic source. The donor can be a healthy human or another patient suffering from the same condition or disease that the patient who is in need of a cell therapy or to which cell therapy will be administered is having.

In some embodiments, the cells obtained from a subject can be a mixture of primary cells, e.g., primary human cells. The samples include tissue, fluid, and other samples taken directly from the subject, as well as samples resulting from one or more processing steps, such as separation, centrifugation, washing, incubation and/or culturing. The biological sample can be a sample obtained directly from a biological source or a sample that is processed. Biological samples include, but are not limited to, body fluids, such as blood, plasma, serum, tissue and organ samples such as spleen, including processed samples derived therefrom. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources. The cells in some embodiments can be obtained from a xenogeneic source, for example, from mouse, rat, non-human primate, and pig.

In some embodiments, the cells to be cultured according to the methods disclosed herein can be derived from existing cell lines, e.g., T cell lines.

In some embodiments, isolation of the cells or populations for culturing can include one or more preparation and separation steps. In some embodiments, cells can be washed, centrifuged, and/or incubated in the presence of one or more reagents, for example, to remove unwanted components, enrich for desired components, lyse or remove cells sensitive to particular reagents. In some embodiments, cells are separated based on one or more property, such as density, adherent properties, size, sensitivity, surface marker expression profile, and/or resistance to particular components.

In some embodiments where blood cells are collected from a subject, the collated blood cells can be washed, e.g., to remove the plasma fraction and to place the cells in an appropriate buffer or media for subsequent processing steps. In some embodiments, the cells can be resuspended in a variety of biocompatible buffers known in the art after washing. In certain embodiments, components of a blood cell sample can be removed and the cells can be resuspended in culture media. In some embodiments, the methods can include density-based cell separation methods, such as the preparation of white blood cells from peripheral blood by lysing the red blood cells and centrifugation.

In some embodiments, the methods can include a step of separating different cell types based on the expression or presence in the cell of one or more specific molecules, such as surface markers, e.g., surface proteins. In some embodiments, any known method for separation based on such markers can be used. In some embodiments, the separation can be affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some embodiments, one or more of subtypes of T cells can be further enriched. In some embodiments, subtypes of T cells can be determined by the presence or level of one or more particular markers, such as surface markers on the T cells. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the $CD8^+$ cells or the T cells, e.g., $CD3^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, CD8+ T cells are enriched for cells positive for CD45RO (or negative for CD45RA) and for CD62L.

In some embodiments, a desired cell population described herein can be collected and enriched (or depleted) via flow cytometry, in which cells stained for multiple cell surface markers are carried in a fluidic stream. In some embodiments, primary T cell populations or the produced T cells can be collected and enriched (or depleted) via preparative scale (FACS)-sorting. In some embodiments, the antibodies or binding partners are labeled with one or more detectable marker, to facilitate separation for positive and/or negative selection. For example, separation can be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

The separation needs not result in 100% enrichment or removal of a particular cell population or cells expressing a particular marker. For example, selection of or enrichment for cells of a particular type, such as those expressing a marker, refers to increasing the number or percentage of such cells, but need not result in a complete absence of cells not expressing the marker. For example, in some embodiments, a selection of $CD3^+$ T cell population enriches for said population, but also can contain some residual or small percentage of other non-selected cells, which can, in some cases, include the other of non-$CD3^+$ T cell and/or non-T cell population still being present in the enriched population. In some embodiments, the T cells having reduction of surface fucosylation can have human peripheral T cells.

In some embodiments, separation or enrichment of specific types of cells can be performed before or after a step of culturing a population of cells in a culture medium. Therefore, in some examples, a mixture of primary cells isolated from a sample can be processed to separate or enrich T cells and remove (e.g. reduce a number of) other types of cells or components (e.g. platelets and red blood cells). Then the enriched population of T cells can proceed to the culturing. Alternatively, in other examples, a mixture of cells containing T cells and other types of cells or components as isolated from a sample can be cultured in a culture medium, without substantially separating or enriching T cells. After the cell population reaches to a desired number or the culturing step is substantially completed, the cultured cells can be processed to separate or enrich T cells for a later use, e.g. adoptive cell therapy or cancer treatment.

In some embodiments, the provided methods can include one or more of various steps for culturing cells and cell populations. In some embodiments, the methods can include one or more steps of culturing a population of cells isolated from a sample or obtained from an existing cell line. In some alternative embodiments, the methods can include one or more steps of culturing a population of cells which was separated from a mixture of cells as obtained and isolated from a sample or obtained from an existing cell line. In some of such embodiment, a majority of the population of cells (e.g. at least 20% or more of the total population of cells) to be cultured can include T cells that were separated or enriched from an earlier population of cells.

In some embodiments, a plurality of cells to be cultured can be generally cultured in a vessel, such as the same unit, chamber, well, column, tube, tubing set, valve, vial, culture dish, bag, or other container for culture or cultivating cells.

The culturing steps can include at least one or more of the following: culture, cultivation, stimulation, activation, propagation, including by incubation in the presence of stimulating conditions, for example, conditions designed to induce proliferation, expansion, activation, and/or survival of cells in the population.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, one or more agents that are designed to modify the cells' characteristics can be added to a culture medium. For example, one or more fucose analog can be added to a culture medium so as to modify a level of fucosylation on the surface of cells, in particular T cells.

In some embodiments, the methods disclosed herein include modifying T cells by culturing the T cells in the presence of a fucose analog. The fucose analog can be added into a cell culture medium. In certain embodiments, the cell culture medium can contain the fucose analog at a concentration of about 1 ng/mL to several mg/mL of culture medium. In some embodiments, the culture medium can contain the fucose analog at a concentration of about 1 ng/mL, about 10 ng/mL, about 50 ng/mL, about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about about 950 ng/mL, about 1 µg/mL, about 10 µg/mL, about 50 µg/mL, about 100 µg/mL, about 150 µg/mL, about 200 µg/mL, about 250 µg/mL, about 300 µg/mL, about 350 µg/mL, about 400 µg/mL, about 450 µg/mL, about 500 µg/mL, about 550 µg/mL, about 600 µg/mL, about 650 µg/mL, about 700 µg/mL, about 750 µg/mL, about 800 µg/mL, about about 950 µg/mL, about 1 mg/mL, about 2 mg/mL, about 3 mg/mL, about 4 mg/mL, about 5 mg/mL of culture medium or more, or any intervening value of the foregoing. In some other embodiments, the cell culture medium can contain the fucose analog of about 1 nM to several mM at its final concentration in a cell culture medium. In some embodiments, the culture medium can contain the fucose analog at a concentration of about 1 nM, about 10 nM, about 50 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about about 950 nM, about 1 µM, about 10 µM, about 50 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about about 950 µM, about 1 mM, about 2 mM, about 3 mM, about 4 mM, about 5 mM or more, or any intervening value of the foregoing at its final concentration in a cell culture medium.

In some embodiments, the methods disclosed herein include activating T cells with one or more T cell activating agents to produce a population of activated T cells. Any combination of one or more suitable T-cell activating agents can be used to produce a population of activated T cells including, but is not limited to, an antibody or functional fragment thereof which targets a T-cell stimulatory or co-stimulatory molecule (e.g., anti-CD2 antibody, anti-CD3 antibody, anti-CD28 antibody, or functional fragments thereof at a concentration of about 1 ng/mL to about 100 ng/mL) a T cell cytokine (e.g., any isolated, wildtype, or recombinant cytokines such as: interleukin 1 (IL-1), interleukin 2, (IL-2), interleukin 4 (IL-4), interleukin 5 (IL-5), interleukin 7 (IL-7), interleukin 15 (IL-15), tumor necrosis factor α (TNF α) at a concentration of about 1 ng/mL to about 100 ng/mL), or any other suitable mitogen (e.g., tetradecanoyl phorbol acetate (TPA), phytohaemagglutinin (PHA), concanavalin A (conA), lipopolysaccharide (LPS), pokeweed mitogen (PWM) at any desired concentration) or natural ligand to a T-cell stimulatory or co-stimulatory molecule at any desired concentration. In some preferred embodiments, an anti-CD3 antibody (or functional fragment thereof), an anti-CD28 antibody (or functional fragment thereof), or a combination of anti-CD3 and anti-CD28 antibodies can be used in accordance with the step of stimulating the population of T lymphocytes.

In some embodiments, the cells are cultured for at or about 1, 2, 3, 4, 5, 6, 7, 8, 9, 10, 11, 12, 13, 14, 15, 16, 17, 18, 19, 20, 21 days or more days before completion of the culturing. In some embodiments, the cells can be subcultured one or more times, i.e. at least some of the cultured cells is transferred from a previous culture medium to a new culture medium before the culturing is completed. In some other embodiment, the cells can be cultured once before the culturing is completed. Any agents added to the culture medium can be provided to the cells once or more times during the entire culturing period.

In some embodiments, the concentration of cultured T cells useful for the methods herein can be about $1.0\text{-}10.0 \times 10^6$ cells/mL. In certain embodiments, the concentration of cultured T cells can be about $1.0\text{-}2.0 \times 10^6$ cells/mL, about $1.0\text{-}3.0 \times 10^6$ cells/mL, about $1.0\text{-}4.0 \times 10^6$ cells/mL, about $1.0\text{-}5.0 \times 10^6$ cells/mL, about $1.0\text{-}6.0 \times 10^6$ cells/mL, about $1.0\text{-}7.0 \times 10^6$ cells/mL, about $1.0\text{-}8.0 \times 10^6$ cells/mL, $1.0\text{-}9.0 \times 10^6$ cells/mL, or about $1.0\text{-}10.0 \times 10^6$ cells/mL. In certain embodiments, the concentration of cultured T cells can be about $1.0\text{-}2.0 \times 10^6$ cells/mL. In certain embodiments, the concentration of cultured T cells can be about $1.0\text{-}1.2 \times 10^6$ cells/mL, about $1.0\text{-}1.4 \times 10^6$ cells/mL, about $1.0\text{-}1.6 \times 10^6$ cells/mL, about $1.0\text{-}1.8 \times 10^6$ cells/mL, or about $1.0\text{-}2.0 \times 10^6$ cells/mL. In certain embodiments, the concentration of lymphocytes can be at least about $1.0 \times 10^6$ cells/mL, at least about $1.1 \times 10^6$ cells/mL, at least about $1.2 \times 10^6$ cells/mL, at least about $1.3 \times 10^6$ cells/mL, at least about $1.4 \times 10^6$ cells/mL, at least about $1.5 \times 10^6$ cells/mL, at least about $1.6 \times 10^6$ cells/mL, at least about $1.7 \times 10^6$ cells/mL, at least about $1.8 \times 10^6$ cells/mL, at least about $1.9 \times 10^6$ cells/mL, at least about $2.0 \times 10^6$ cells/mL, at least about $4.0 \times 10^6$ cells/mL, at least about $6.0 \times 10^6$ cells/mL, at least about $8.0 \times 10^6$ cells/mL, or at least about $10.0 \times 10^6$ cells/mL.

T cells cultured by the methods described above can have reduced surface fucosylation. In some aspects, the reduced surface fucosylation can refer to reduction or inhibition of the level of fucosylation that is naturally present on the surface of normal T cells. In some embodiments, the reduction of surface fucosylation on T cells does not include substitution of naturally present fucose on the T cell surface with the fucose analog that is artificially provided to the T cells.

T cells cultured by the methods described above can have reduced surface fucosylation. In some embodiments, the average surface fucosylation on the T cells cultured and produced by the provided methods can have at least about 5% reduction as compared to the average surface fucosylation of T cells cultured in the absence of a fucose analog, i.e. control T cells. In some embodiments, the average surface fucosylation on the T cells cultured and produced by the provided methods can have at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, about 100% reduction relative to the average surface fucosylation of control T cells that were cultured in the absence of a fucose analog. The level of surface fucosylation on T cells can be determined by techniques available in the art, e.g. flow cytometry.

In some embodiments, the culturing step can be completed and the cultured cells can proceed to a step of collection (or harvesting) of at least some of cultured cells. The culturing step can be completed when the number of cultured cells reaches at a desired number, once a planned period of culturing is passed, and/or if the average surface fucosylation on the culture T cells reaches at a desired level (e.g. at least 5% reduction or more relative to the average surface fucosylation of control T cells).

After the culture step is completed, the cells can be harvested by techniques available in the art. The step of harvest can include one or more steps such as centrifugation, wash, removal of unwanted cells or components, and isolation of desired type of cells as described elsewhere in this paper.

In some embodiments, the population of cells produced by the methods described herein, which include T cells having reduced surface fucosylation, can optionally be cryopreserved so that the cells can be used at a later date, e.g. for administration in an adoptive cell therapy or cancer treatment, or formulation of a pharmaceutical composition for the therapy or treatment. Such a method can include a step of washing and concentrating the population of desired T cells, i.e. T cells having reduced surface fucosylation with a diluent solution. In some embodiments, the diluent solution can contain normal saline, 0.9% saline, PlasmaLyte A, 5% dextrose/0.45% NaCl saline solution, human serum albumin (HSA), or a combination thereof. In some embodiments, HSA can be added to the washed and concentrated cells for improved cell viability and cell recovery after thawing. In another embodiment, the washing solution can be normal saline and washed and concentrated cells can be supplemented with HSA (5%). In some embodiments, a cryopreservation mixture can be generated. The cryopreservation mixture can include the diluted population of cells in the diluent solution and a suitable cryo preservative solution. In some aspects, the cryopreservative solution can be any suitable cryo preservative solution available in the art, mixed with the diluent solution of produced T cells. In some embodiments, the method also includes a step of freezing the cryopreservation mixture. In one aspect, the cryopreservation mixture is frozen in a controlled rate freezer using a defined freeze cycle at any desired cell concentration, e.g. between about $10^6$ to $10^8$ per ml of cryopreservation mixture. The method can also include a step of storing the cryopreservation mixture in vapor phase liquid nitrogen.

In some embodiments, the T cells produced by the methods provided herein, e.g. T cells having reduction of surface fucosylation can be used in an adoptive cell therapy or cancer treatment. For example, the produced T cells can be administered to a subject in need of the therapy or treatment. In some embodiments, the T cells produced by the methods provided herein, e.g. T cells having reduction of surface fucosylation can be used to formulate a pharmaceutical composition that can be used in an adoptive cell therapy or cancer treatment.

II-2. In Vivo Production Methods

In some aspects, in vivo methods of producing T cells having reduced surface fucosylation are provided herein. The methods can include providing a fucose analog to an animal and obtaining T cells having reduced surface fucosylation from the animal. The T cells produced by these methods can have reduced surface fucosylation relative to T cells present in or obtained from an animal that was not provided with a fucose analog. Such T cells produced by the methods disclosed herein can be used for therapeutic purposes such as an adoptive cell therapy or cancer treatment. Therefore, at least in some embodiments, the T cells having reduced surface fucosylation are referred to as "therapeutic T cells".

In some embodiments, the fucose analog used in the methods can be formula (I) or (II):

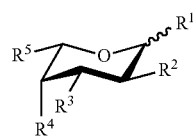

(I)

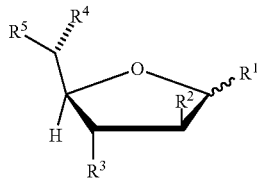

(II)

or a pharmaceutically acceptable salt or solvate form thereof, wherein each of formula (I) or (II) can be the alpha or beta anomer or the corresponding aldose form;
wherein $R^2$ is halogen; each of $R^1$, $R^3$, and $R^4$ is independently —OH or a hydrolyzable ester group; and $R^5$ is —$CH_3$,
or
wherein each of $R^1$, $R^2$, $R^3$, and $R^4$ is independently —OH or a hydrolyzable ester group; and $R^5$ is alkynyl.

In some embodiments, $R^2$ is —F.
In some embodiments, $R^5$ is —C≡CH.
In some embodiments, the fucose analog used in the methods has formula (I) or (II), wherein $R^2$ is halogen; each of $R^1$, $R^3$, and $R^4$ is independently —OH or a hydrolyzable ester group; and $R^5$ is —$CH_3$, or wherein each of $R^1$, $R^2$, $R^3$, and $R^4$ is independently —OH or a hydrolyzable ester group; and $R^5$ is —C≡CH.

In some embodiments, the fucose analog used in the methods has formula (I) or (II), wherein $R^2$ is —F; each of $R^1$, $R^3$, and $R^4$ is independently —OH or a hydrolyzable ester group; and $R^5$ is —$CH_3$, or wherein each of $R^1$, $R^2$, $R^3$, and $R^4$ is independently —OH or a hydrolyzable ester group; and $R^5$ is —C≡CH.

In some selected embodiments of formula (I) or (II), $R^2$ is halogen; each of $R^1$, $R^3$, and $R^4$ is independently —OH or a hydrolyzable ester group; and $R^5$ is —$CH_3$. In some selected embodiments of formula (I) or (II), $R^2$ is —F; each of $R^1$, $R^3$, and $R^4$ is independently —OH or a hydrolyzable ester group; and $R^5$ is —$CH_3$.

In some selected embodiments of formula (I) or (II), each of $R^1$, $R^2$, $R^3$, and $R^4$ is independently selected from —OH, or a hydrolyzable ester group; and $R^5$ is —C≡CH.

In some embodiments, the hydrolyzable ester group is —OC(O)$C_1$-$C_{10}$ alkyl. In some selected embodiments, the hydrolyzable ester group is —OC(O)$CH_3$.

In some selected embodiments of formula (I) or (II) wherein $R^2$ is —F, each of $R^1$, $R^3$ and $R^4$ is independently selected from the group consisting of —OH and —OC(O) $C_1$-$C_{10}$ alkyl. In some selected embodiments of formula (I) or (II) wherein $R^2$ is —F, each of $R^1$, $R^3$ and $R^4$ is independently selected from the group consisting of —OH and —OC(O)$CH_3$. In one specific embodiment of formula (I) or (II), $R^2$ is —F and each of $R^1$, $R^3$ and $R^4$ is —OH.

In some selected embodiments of formula (I) or (II) wherein $R^5$ is —C≡CH, each of $R^1$, $R^2$, $R^3$ and $R^4$ is independently selected from the group consisting of —OH and —OC(O)$C_1$-$C_{10}$ alkyl. In some selected embodiments of formula (I) or (II) wherein $R^5$ is —C≡CH, each of $R^1$, $R^2$, $R^3$ and $R^4$ is independently selected from the group consisting of —OH and —OC(O)$CH_3$. In one specific embodiment of formula (I) or (II), $R^5$ is —C≡CH and each of $R^1$, $R^2$, $R^3$ and $R^4$ is —OH. In another specific embodiment of formula (I) or (II), $R^5$ is —C≡CH and each of $R^1$, $R^2$, $R^3$ and $R^4$ is —OAc.

In some selected embodiments, the fucose analog used in the methods has the formula:

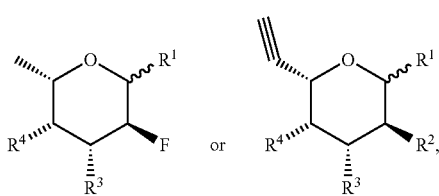

or an aldose form thereof, wherein each of $R^1$, $R^2$, $R^3$, and $R^4$ is as defined and described herein.

In some selected embodiments, the fucose analog is 2-deoxy-2-fluoro-L-fucose.

In some selected embodiments, the fucose analog is alkynyl fucose peracetate. Alkynyl fucose peracetate can be alkynyl fucose tetraacetate, alkynyl fucose triacetate, alkynyl fucose diacetate, alkynyl fucose monoacetate, or combinations thereof. In one exemplified embodiment, the fucose analog is (3S,4R,5R,6S)-6-ethynyltetrahydro-2H-pyran-2,3,4,5-tetrayl tetraacetate or 5-((S)-1-hydroxyprop-2-yn-1-yl)tetrahydrofuran-2,3,4-triyl triacetate.

In any of the various embodiments, the endocylic ring oxygen of the fucose analog of formulae (I) and (II) can be replaced by sulfur.

The methods provided herein can contain a step of providing a fucose analog to an animal. The provision of a fucose analog to an animal can be done via various ways of administration. The fucose analog in some embodiments can be administered to an animal using standard administration techniques, including oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection. In some embodiments, the fucose analog can be administered orally to an animal.

In some embodiments, the methods disclosed herein produce T cells having reduced surface fucosylation which can be used in an adoptive cell therapy or cancer treatment for a subject in need of such therapy or treatment.

In some embodiments, the cell therapy, e.g., adoptive cell therapy or cancer treatment using T cells, can be carried out by autologous transfer, in which the cells are isolated and/or otherwise prepared from a subject who is to receive the cell therapy or treatment, or from a sample derived from such a subject. Thus, in some aspects, a fucose analog can be provided or administered to a subject, e.g., patient, in need of a treatment and the resulting T cells with reduced surface fucosylation, following isolation and processing are administered to the same subject.

In some embodiments, the cell therapy, e.g., adoptive cell therapy or cancer treatment using T cells, can be carried out by allogeneic transfer, in which the cells are isolated and/or otherwise prepared from a subject other than a subject who is to receive or who ultimately receives the cell therapy or treatment, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the first and second subjects are genetically different. In some embodiment, the first and second subjects do not belong to a same species, e.g. the first subject is a human and the second subject is a non-human animal. The T cells obtained from the second subject can be isolated and processed for the therapy or treatment of the first subject.

An effective amount of a fucose analog can be provided to an animal. The effective amount can refer to an amount of the fucose analog that is sufficient to provide a desired result, i.e. production of T cells with reduced surface fucosylation. In some embodiments, an effective amount of fucose analog can be in the range from about 1 to about 500 mg/kg of body weight of the fucose analog. In some embodiments where a fucose analog is provided or administered orally, e.g. via feeding with food or water, the oral dosage of fucose analog administered to an animal can be about 1 mg/kg to about 1 g/kg of the animal's body weight, more typically about 5 mg/kg, 10 mg/kg, 20 mg/kg, 30 mg/kg, 40 mg/kg, or 50 mg/kg to about 1 g/kg of the animal's body weight. In some aspects, the dosage administered to an animal is about 1 g, about 5 g, or about 10 g to about 150 g per day, or from about 1 g, about 5 g, about 10 g, about 15 g or about 20 g to about 60 g per day. In some embodiments, a fucose analog can be provided with food or water at any desired amount that is suitable to induce reduction of surface fucosylation in the animal fed with the fucose analog.

A fucose analog used in the methods described herein in some embodiments can be coadministered to an animal with one or more additional pharmaceutically acceptable excipient or carrier, either simultaneously or sequentially in any order.

In some embodiments, a fucose analog or a composition thereof can be administered on for a certain period, e.g. one to several days, one to several weeks, one to several months or longer, with or without interruption. In some embodiments, a fucose analog or a composition thereof can be administered a daily, weekly, biweekly or monthly schedule.

In some embodiments, the provision or administration of a fucose analog to an animal can be completed when a desired result is achieved, for example, the average surface fucosylation of T cells obtained from the animal is reduced by any number of percentage, e.g. between about 5% to about 95% relative to control T cells.

The methods provided herein can include a step of obtaining a mixture of cell, e.g. T cells from the animal provided with a fucose analog. The obtained cells can include T cells with reduced surface fucosylation.

T cells cultured by the methods described above can have reduced surface fucosylation. In some aspects, the reduced surface fucosylation can refer to reduction or inhibition of the level of fucosylation that is naturally present on the surface of normal T cells. In some embodiments, the reduction of surface fucosylation on T cells does not include substitution of naturally present fucose on the T cell surface with the fucose analog that is artificially provided to the T cells.

T cells produced by the methods described above can have reduced surface fucosylation. In some embodiments, the average surface fucosylation on the T cells obtained from an animal that was provided with a fucose analog can have at least about 5% reduction as compared to the average surface fucosylation of T cells present or obtained from an animal that was not provided with a fucose analog, i.e. control T cells. In some other embodiments, the average surface fucosylation on the T cells obtained from an animal that was provided with a fucose analog can have at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, about 100% reduction relative to the average surface fucosylation of control T cells that are present or obtained from an animal that was not provided with a fucose analog for at least several hours, several days, several weeks, several months or more before the control T cells were tested or obtained. The level of surface fucosylation on T cells can be determined by techniques available in the art, e.g. flow cytometry.

In some embodiments, the T cells and cell populations can be isolated from a sample, such as a biological sample from or derived from an animal provided with a fucose analog. The samples can include tissue, fluid, and other samples taken directly from the animal. The biological sample can be a sample obtained directly from a biological source or a sample that is processed. Biological samples include, but are not limited to, body fluids, such as blood, plasma, serum, tissue and organ samples such as spleen, including processed samples derived therefrom. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom.

In some embodiments, after the T cells and cell populations are obtained from an animal, there can be one or more processing steps, such as separation, centrifugation, washing, incubation and/or culturing of the obtained cells. In some embodiments, the obtained cell population containing T cells can be processed to isolate or enrich T cells and remove (or reduce) a number of other types of cells (e.g. red blood cells) and/or components (e.g. platelets). In some embodiments, the obtained cell population or the further enriched T cells can be cultured in a cell culture medium using techniques available in the art so as to maintain the cells and/or increase the cell number sufficient for a later use, e.g. adoptive cell therapy or cancer treatment, or formulation of pharmaceutical compositions. In some embodiments, the T cells with reduced surface fucosylation as obtained from the animal or further cultured after isolation from the animal can be stored for a later usage, e.g. by cryopreservation techniques available in the art or as described elsewhere in this paper, In some embodiments, the T cells having reduction of surface fucosylation which are produced by the in vivo production methods described herewith can be used in an adoptive cell therapy or cancer treatment. In some embodiments, the produced T cells as obtained from an animal or further cultured after the isolation from the animal can be administered to a subject in need of such therapy or treatment. In some embodiments, the produced T cells as obtained from an animal or further cultured after the isolation from the animal can be used to formulate a pharmaceutical composition that can be used in an adoptive cell therapy or cancer treatment. In some embodiments, the animal is a human.

The production methods described herein can further comprise a step of modifying a population of T cells. For example, the T cell population can be transduced with a viral vector comprising a nucleic acid molecule which encodes the cell surface receptor to produce a population of transduced T cells. Several recombinant viruses have been used as viral vectors to deliver genetic material to a cell. Viral vectors that can be used in accordance with the transduction step can be any ecotropic or amphotropic viral vector including, but not limited to, recombinant retroviral vectors, recombinant lentiviral vectors, recombinant adenoviral vectors, and recombinant adeno-associated viral (AAV) vectors. Any suitable growth media and/or supplements for growing viral vectors can be used in the viral vector inoculum in accordance with the methods known in the art. In one embodiment, the viral vector comprises a heterologous gene encoding a cell surface receptor. In one particular embodiment, the cell surface receptor is capable of binding an antigen on the surface of a target cell, e.g., on the surface of a tumor cell.

IV. PHARMACEUTICAL COMPOSITIONS FOR ADOPTIVE CELL THERAPY OR CANCER TREATMENT

Cell populations or T cells having reduced surface fucosylation that are produced by the above-described production methods can be formulated for use in adoptive cell therapy or cancer treatment. The desired T cells (or therapeutic T cells), i.e. T cells having reduced surface fucosylation or a mixture of cells having such T cells can be formulated as pharmaceutical compositions comprising a therapeutically or prophylactically effective amount of the desired T cells and one or more pharmaceutically compatible (acceptable) ingredients. In some aspects, pharmaceutical compositions of the therapeutic T cells and pharmaceutical excipients can be provided in which an effective amount of the T cells is in admixture with the excipients, suitable for administration to a subject. In preferred aspects, the T therapeutic cells and pharmaceutical composition thereof is formulated for administration to a human. Accordingly, the present disclosures provide a pharmaceutical composition comprising T cells with reduced surface fucosylation formulated for administration to a human. The formulated composition can generally comprise one or more pharmaceutically compatible (acceptable) excipients or carriers.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the manner of administration, the composition employed, and the severity of the disease or condition being treated.

The pharmaceutical compositions according to the disclosures herein can be in the form of a liquid, e.g., an elixir, syrup, solution, emulsion or suspension. In some embodiments, the liquid can be useful for delivery by injection. In a composition for administration by injection (as described above), one or more of a surfactant, preservative, wetting agent, dispersing agent, suspending agent, buffer, stabilizer and isotonic agent can also be included.

The pharmaceutical compositions described herein can be in any form that allows for the composition to be administered to an animal (e.g., a human). Typical routes of administration include, without limitation, oral, parenteral, and sublingual. Parenteral administration includes subcutaneous injections, intraperitoneal injections, intravenous, intramuscular, intrasternal injection or infusion techniques. These pharmaceutical compositions can be formulated so as to allow T cells with reduced surface fucosylation to be effective upon administration of the composition to a subject in need of the therapy or treatment.

V. THERAPEUTIC METHODS

In some aspects, methods of providing an adoptive cell therapy to a subject are provided herein. The methods can include administering T cells with reduced surface fucosylation to the subject in need of the cell therapy.

In some embodiments, the methods disclosed herein provide an adoptive cell therapy to a subject. The provision of an adoptive cell therapy to a subject can include a step of administering a mixture of cells, which includes T cells having reduced surface fucosylation (i.e. therapeutic T cells), to a subject. In some embodiments, the subject can be in need to such therapy. In some embodiments, the provision of an adoptive cell therapy to a subject can also include a step of producing the therapeutic T cells for the therapy according to any of in vitro and in vivo methods described elsewhere in this paper.

In some embodiments, an adoptive cell therapy can be selected from the group consisting of tumor-infiltrating lymphocyte (TIL) immunotherapy, autologous cell therapy, engineered autologous cell therapy (eACT™), allogeneic T cell transplantation, non-T cell transplantation, and any combination thereof. In some embodiments, adoptive cell therapy can broadly include any method of selecting, enriching in vitro, and administering to a patient autologous or allogeneic T cells that recognize and are capable of binding tumor cells. TIL immunotherapy is a type of adoptive T cell therapy, wherein lymphocytes capable of infiltrating tumor tissue are isolated, enriched in vitro, and administered to a patient. The TIL cells can be either autologous or allogeneic. Autologous cell therapy is an adoptive T cell therapy that involves isolating T cells capable of targeting tumor cells from a patient, enriching the T cells in vitro, and administering the T cells back to the same patient. Allogeneic T cell transplantation can include transplant of naturally occurring T cells expanded ex vivo or genetically engineered T cells. Engineered autologous cell therapy is an adoptive T cell therapy wherein a patient's own lymphocytes are isolated, genetically modified to express a tumor targeting molecule, expanded in vitro, and administered back to the patient. Non-T cell transplantation can include autologous or allogeneic therapies with non-T cells such as, but not limited to, natural killer (NK) cells.

In some aspects, methods of treating a cancer are provided herein. The methods can include administering T cells with reduced surface fucosylation to a subject in need of such treatment. In some embodiments, the methods can also include a step of producing the therapeutic T cells for the treatment according to any of in vitro and in vivo methods described elsewhere in this paper.

In some aspects, T cells used in adoptive cell therapy or cancer treatment according to the methods disclosed herein are therapeutic T cells that have reduced surface fucosylation relative to control T cells. In some aspects, the reduced surface fucosylation can refer to reduction or inhibition of the level of fucosylation that is naturally present on the surface of normal T cells. In some embodiments, the reduction of surface fucosylation on T cells does not include substitution of naturally present fucose on the T cell surface with the fucose analog that is artificially provided to the T cells.

As described earlier, in some embodiments the T cells with reduced surface fucosylation used in adoptive cell therapy or cancer treatment can originate from the same subject who will receive the therapy or treatment, i.e. autologous therapy or treatment, or from a subject who is different from the subject who will be receive the therapy or treatment, i.e. allogenic therapy or treatment.

In some aspects, T cells used in adoptive cell therapy or cancer treatment according to the methods disclosed herein are therapeutic T cells that have reduced surface fucosylation relative to control T cells. In some embodiments, in particular where an autologous therapy or treatment is administered to a human patient, T cells derived from the same patient can be processed according to the in vitro or in vivo methods disclosed herein to produce the therapeutic T cells. In such embodiments, control T cells can refer to (1) a population of T cells present or obtained from a normal, healthy human or (2) a population of T cells which were present or obtained from the same patient prior to the production of therapeutic T cells. In some other embodiments, in particular where an allogenic therapy or treatment is administered to a human patient, T cells derived from a donor that is not the patient can be processed according to the in vitro or in vivo methods disclosed herein to produce the therapeutic T cells. In such embodiments, control T cells can refer to a population of T cells which were present or obtained from the donor prior to the production of therapeutic T cells. In some other embodiments, where an allogenic therapy or treatment is administered to a human patient and therapeutic T cells used in the therapy or treatment originate from a non-human animal (i.e. a donor animal), control T cells can refer to (1) a population of T cells present or obtained from a normal, healthy non-human animal or (2) a population of T cells which were present or obtained from the donor animal prior to the production of therapeutic T cells.

In some embodiments, the average surface fucosylation on the T therapeutic cells used in adoptive cell therapy or cancer treatment according to the methods disclosed herein can have at least about 5% reduction as compared to the average surface fucosylation of control T cells. In some other embodiments, the average surface fucosylation on the T cells obtained from an animal that was provided with a fucose analog can have at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, about 100% reduction relative to the average surface fucosylation of control T cells. The level of surface fucosylation on T cells can be determined by techniques available in the art, e.g. flow cytometry.

In some aspects, the methods disclosed herein for providing an adoptive cell therapy or treating a cancer intend to treat any diseases, conditions, and disorders including, but not limited to, carcinoma of the breast, esophageal cancer, colorectal, pancreas, stomach, GIST, hepatocellular, liver, lung, small cell lung, ovarian, uterine, cervix, bladder, renal, colon, small intestine, large intestine, gastric cancer, lymphoma, prostate, testis, thyroid carcinoma, malignant melanoma, uveal melanoma, multiple myeloma, mesothelioma, osteosarcoma, chondrosarcoma, myosarcoma, glioblastoma, sarcoma, glioma, or other brain tumors, head/neck other gastrointestinal and germ cell tumors, haematologic malignancies, leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of skin (including melanoma), bone cancers, epithelial cancers, renal cell carcinoma, pancreatic adenocarcinoma, Hodgkin lymphoma, glioblastoma, neuroblastoma, Ewing sarcoma, medulloblastoma, synovial sarcoma, and/or mesothelioma.

In some aspects, the methods disclosed herein for providing an adoptive cell therapy or treating a cancer have a step of administering T cells with reduced surface fucosylation, i.e. therapeutic T cells to a subject. In some embodiments, the therapeutic T cells can be formulated, optionally with one or more pharmaceutically acceptable ingredients, in form of pharmaceutical compositions as described herein to be administered to an animal (e.g., a human). In some aspects, the therapeutic T cells or pharmaceutical compositions thereof can be administered, without limitation, oral, parenteral, and sublingual. Parenteral administration includes subcutaneous injections, intraperitoneal injections, intravenous, intramuscular, intrasternal injection or infusion techniques. These pharmaceutical compositions can be formulated so as to allow T cells with reduced surface fucosylation to be effective upon administration of the composition to an animal.

In some embodiments, the therapeutic T cells or pharmaceutical compositions containing the therapeutic T cells can be administered (e.g. injected) at a site or in vicinity of cancer cells, i.e. local administration. For example, if a cancer is found in an organ (e.g. a liver), the pharmaceutical compositions can be injected to which cancer cells are found in the liver or in close proximity of the cancer cells (e.g. between several millimeters to several centimeters from a boundary of the cancer cells). In alternative embodiments, the therapeutic T cells or pharmaceutical compositions can be administered (e.g. injected) to a patient's circulating system (e.g. blood vessels), i.e. a systematic administration such that the therapeutic T cells can reach at a target site(s) where pathological cells are present via the patient's circulating system. In some embodiments, the therapeutic T cells can further have a component that specifically binds a cell surface antigen of a cell or disease to be targeted, such as a tumor cell or a cancer cell. Therefore, the therapeutic T cells can reach at and exhibit therapeutic effect to target cells with specificity after being delivered via the circulating system.

In some embodiments, T cells having reduced surface fucosylation, i.e. therapeutic T cells or pharmaceutical compositions thereof can be administered in an amount that is effective to obtain a desired result or effect, e.g. treating the disease or condition, such as a pharmaceutically effective amount. Thus, in some embodiments, the methods of administration include administration of the therapeutic T cells or pharmaceutical compositions thereof at effective amounts to a subject in need of adoptive cell therapy or cancer treatment. Therapeutic efficacy in some embodiments can be monitored by periodic assessment of treated subjects. For repeated administrations over several days or longer, depending on the condition, the treatment is repeated until a desired suppression of disease symptoms occurs. In some embodiments, other dosage regimens can be useful and can be determined. The desired dosage can be delivered by a single administration of the therapeutic T cells or pharmaceutical compositions thereof, by multiple administrations, or by continuous administration.

In some embodiments, T cells having reduced surface fucosylation, i.e. therapeutic T cells or pharmaceutical compositions thereof can be administered in an amount that is effective to obtain a desired result or effect, e.g. treating the disease or condition to a subject in need of such therapy or treatment. The desired result or effect aimed to achieve by the administration of the therapeutic T cells or pharmaceutical compositions thereof according to the methods described herein can include one or more of the following outcomes compared to prior to the administration:

(i) a reduction in lesions (target and/or non-target lesions, as measured by CT scan or physical exam for apparent lesions, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to prior to the administration of the therapeutic T cell or pharmaceutical compositions thereof);

(ii) a dissipation (i.e., reduction) of cancer metastases, as measured by biopsy, magnetic resonance imaging, or other suitable methods, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to prior to the administration of the therapeutic T cell or pharmaceutical compositions thereof);

(iii) a reduction in tumor burden (e.g., number of cancer cells, the size of a tumor, or the amount of cancer in the body) of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to prior to the administration of the therapeutic T cell or pharmaceutical compositions thereof);

(iv) an increase in progression-free survival (PFS), of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to prior to the administration of the therapeutic T cell or pharmaceutical compositions thereof); and/or (v) an increase in overall survival (OS), of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to expected overall survival).

In some embodiments, T cells having reduced surface fucosylation (i.e. therapeutic T cells) or pharmaceutical compositions thereof can be administered at a pharmaceutically effective amount, i.e. an amount that is effective to obtain a desired result or effect, e.g. treating the disease or condition. In some aspects, the pharmaceutically effective amount can include a desired dose or number of therapeutic T cells and/or a desired ratio of such T cells with other types of cells. Thus, the dosage of cells in some embodiments is based on a total number of cells (or number per kg body weight) and a desired ratio of the individual populations or sub-types, such as the $CD3^+$ to non-$CD3^+$ ratio. In some embodiments, the dosage of cells is based on a desired total number (or number per kg of body weight) of cells in the individual populations or of individual cell types contained in the pharmaceutical compositions. In some embodiments, the dosage is based on a combination of such features, such as a desired number of total cells, desired ratio, and desired total number of therapeutic T cells in the individual populations.

In some embodiments, the desired dose or amount is a desired number of therapeutic T cells or a desired number of therapeutic T cells per unit of body weight of the subject to whom the cells are administered, e.g., cells/kg. In some aspects, the desired dose or amount is at or above a minimum number of therapeutic T cells or minimum number of therapeutic T cells per unit of body weight.

In certain embodiments, therapeutic T cells can be administered to a subject at a range of about one hundred to about 100 billion cells, such as, e.g., about several hundred to about several thousand cells, about several thousand to about 1 million cells, about 1 million to about 50 billion cells (e.g., about 1 hundred cells, about 5 hundred cells, about 1 thousand cells, about 5 thousand cells, about 1 million cells, about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. The foregoing effective doses or amounts of therapeutic T cell can be per individual administration or per entire duration of therapy or treatment.

In some embodiments, the dose or amount of therapeutic T cells can be within a range of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the therapeutic T cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. The foregoing effective doses or amounts of therapeutic T cell can be per individual administration or per entire duration of therapy or treatment.

In some embodiments, T cells with reduced surface fucosylation, i.e. therapeutic T cells or a pharmaceutical composition thereof can be administered on a daily, weekly, biweekly or monthly schedule, according to a desired effect. In some aspects, the therapeutic T cells or pharmaceutical compositions thereof can be administered from about 1 to 5, about 1 to about 10, about 1 to about 15, or more cycles, wherein each cycle is a month in duration. The doses within each cycle can be given on daily (including once daily, twice daily, or more than twice daily), every other day, twice weekly, weekly, bi-weekly, once every three weeks or monthly basis. A cycle can optionally include a resting period. Alternatively, a resting period can be included between cycles. In some aspects, administration will be for the duration of the disease.

In some aspects, the methods disclosed herein can further comprise the administration of T cells having surface fucosylation, i.e. therapeutic T cells or pharmaceutical compositions thereof and an additional therapeutic agent or pharmaceutically acceptable salts or solvates thereof. The therapeutic T cells or pharmaceutical compositions thereof and the therapeutic agent can act additively or, more preferably, synergistically. In a preferred embodiment, the therapeutic T cells or pharmaceutical compositions thereof can be administered concurrently with the administration of one or more therapeutic agent(s), which can be part of the same composition or in a different composition from that comprising the therapeutic T cells. In another embodiment, the therapeutic T cells or pharmaceutical compositions thereof can be administered prior to or subsequent to administration of the therapeutic agent(s).

In some aspects, the amount of T cells having reduced surface fucosylation, i.e. therapeutic T cells or pharmaceutical compositions thereof that is effective in the methods described herein will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

VI. KITS FOR THERAPEUTIC USE

In some aspects, kits for use in adoptive cell therapy or cancer treatment are provided. Such kits can include a pharmaceutical composition that comprises T cells having reduced surface fucosylation, i.e. therapeutic T cells, and a pharmaceutically acceptable carrier.

In some embodiments, the kit can include instructions for use in any of the therapeutic methods described herein. The included instructions can provide a description of administration of the pharmaceutical compositions to a subject to achieve the intended activity, e.g., treatment of a disease or condition such as cancer, in a subject. In some embodiments, the instructions relating to the use of the pharmaceutical compositions described herein can include information as to dosage, dosing schedule, and route of administration for the intended treatment. The containers can be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

In some embodiments, the kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. In some embodiments, a kit can have a sterile access port (for example, the container can be an intravenous solution bag or a vial having a stopper pierceable by a hypodermic injection needle).

VII. EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1—A20 Mouse Lymphoma Study with Adoptive Transfer of Splenocytes

The immunogen, KLH-A20 Id Fab, was generated as follows. A20 tumor Ig heavy- and light-chain variable regions were cloned by PCR amplification and ligated into a mouse IgG expression vector for A20 Id production in HEK293F17 cells. The A20 Id murine antibody was purified by Protein A. Concentrated antibody (20 mM KPO4, 10 mM EDTA, pH 7.0) was treated with four volumes of immobilized papain resin (with 20 mM cysteine) at 37° C. overnight. Resin was removed and the supernatant incubated with Protein A resin overnight (4° C.), followed by filtration to remove the resin-bound antibody Fc. Fab-containing flow-through was collected, dialyzed, and concentrated in PBS solution, pH 7.4. Fab conjugation was accomplished by using mariculture KLH (mcKLH) and NHS-PEG12-maleimide. mcKLH in PBS solution, pH 8.0 (10 mg/mL), was mixed and incubated with NHS-PEG12-maleimide (125 mM final, 37° C., 20 min). The product mcKLHPEG12-maleimide was buffer-exchanged on a PD10 column (PBS solution, pH 7.4) and concentrated to 5 mg/mL. The A20 Id Fab (4 mg/mL) was reduced with (tris(2-carboxyethyl) phosphine (5 mM) in 2 mM EDTA-containing buffer (30 min, 37° C.). Reducing agent was removed via PD10 column (PBS solution, pH 7.4, 5 mM EDTA), and reduced Fab was concentrated to 5 mg/mL, mixed with the KLH-PEG12-maleimide (3:1 molar ratio, Fab:KLH), and incubated at room temperature (1 h). Excess maleimide cross-linker was quenched with N-acetylcysteine and removed by PD10 column (PBS solution, pH 7.4).

Donor mice for an adoptive transfer of splenocytes were produced as described below. A20 cells (ATCC) were cultured in RPMI 1640 with 10% FBS, 10 mM HEPES, 1 mM sodium pyruvate, 50 µM 2-mercaptoethanol and penicillin (100 U/ml)/streptomycin (100 µg/ml) (PS). Mice (BALB/c, Harlan) were injected subcutaneously with the KLH-A20 Id Fab conjugate (50 µg) with TiterMax adjuvant (1:1) on day −21 with a boost on day −7. The 2FF treatment group received drinking water containing 20 mM 2FF beginning on day −14 while the untreated group received plain water. One week after the second vaccination (day 0), all mice received irradiated A20 tumor cells (RS2000 irradiator level 4, 17 mins, $2.5 \times 10^6$ cells per mouse i.v.). 2FF treatment continued until day 14. Splenocytes harvested from each group of donor mice (day 14) were adoptively transferred (once) to naïve mice ($50 \times 10^6$ cells/mouse). One group received cells from donor mice that had received 2FF and one group of mice received cells from donor mice that were not treated with 2FF (n=7/group). Both were then challenged with live A20 cells the day after transfer ($2.5 \times 10^6$ cells). A control group received no treatments. Splenocytes transferred from donor mice that did not receive 2FF provided increased survival compared to naïve animals (increased from 27 days to 35 day median survival), while splenocytes transferred from donor mice that received 2FF provided a further increase in median survival to 43 days. This suggests that adoptive transfer of cells from animals treated with 2FF can provide enhanced antitumor activity over adoptive transfer of cells from animals that did not receive 2FF.

Example 2—A20 Mouse Lymphoma Study with Adoptive Transfer of CD3+ T-Cells

Figure 2:
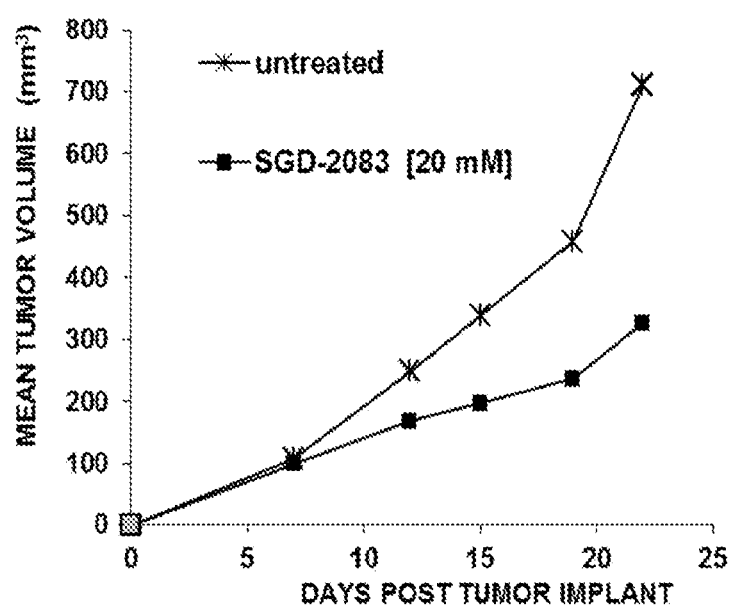
FIG. 2 shows a graph demonstrating in vivo effects of 2FF on the growth of SQ implanted A20 mouse lymphoma cells in naïve BALB/c mice that were used to generate isolated Cd3+ T cells.

20 Balb/c mice were implanted with A20 cells (0.2 mL of $5 \times 10^{\wedge}6$ cells s.c./mouse), one group of mice consisting of 10 animals received 2FF (20 mM in drinking water) from day 0 to termination of study. A20 lymphoma tumors were allowed to grow out and mice sacrificed after 20 days. As previously shown, mice receiving 20 mM of 2FF had a significant delay in tumor progression compared to animals in the control group (FIG. 2).

Reduction of Surface Fucosylation on CD3+ T Cells Upon Treatment of 2FF

Figure 3:
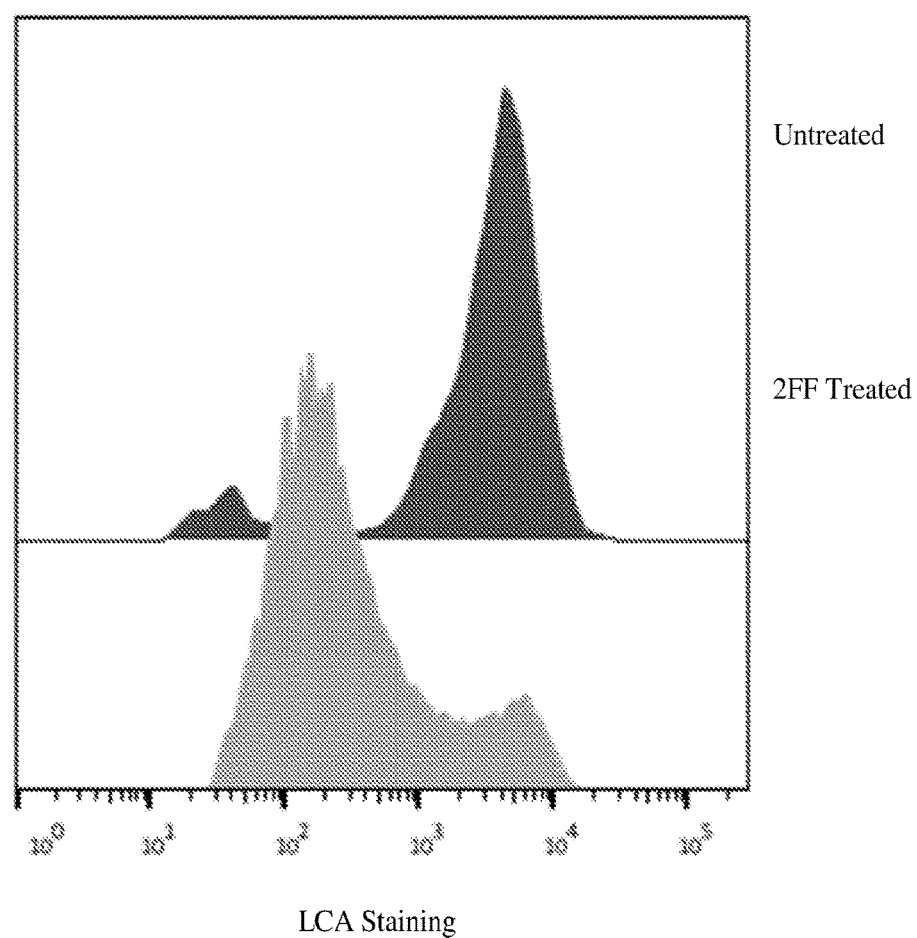
FIG. 3 shows a graph demonstrating reduced surface fucosylation of CD3+ T cells isolated from A20 tumor bearing mice treated with 20 mM 2FF as determined by surface LCA staining.

Mice from the untreated and 2FF treated group were sacrificed and spleens taken for CD3 T-cell enrichment. In brief spleens were collected in RPMI containing 2% FBS and cell suspensions passed through a 70 µm mesh nylon strainer washed with 2% RPMI. Cells were suspended in 10 mls of ACK lysis buffer and incubate for 5 min in this buffer to get rid of RBCs. Cells were centrifuged at 300×g for 5 minutes and re-suspended in PBS containing 2% FBS and 1 mM EDTA. T-cells were isolated using EasySep mouse T cell isolation kit as per the manufactures recommendation. Briefly, cells were re-suspended at $10^8$ cells/mL to which 50 µL/mL of rat serum was added. Cells were then transferred into a 5 mL polystyrene tube and 50 µL of isolation cocktail added to the sample followed by room temperature incubation for 10 minutes. Rapid spheres were vortexed and 75 µL/mls added followed by room temperature incubation for 2.5 minutes. Sample volume was topped off to 2.5 mL and incubated with the cell isolation magnet for 2.5 minutes. The magnet was inverted and CD3$^+$ T cells collected and washed twice in RPMI and resuspended at $21.2 \times 10^6$ cells/ml. Cells were checked for their fucosylation state by flow cytometry and the isolated from 2FF treated animals displayed a significant reduction in surface fucosylation (FIG. 3).

Anti-Tumor Activity of T Cells with Reduced Surface Fucosylation

To assess the anti-tumor activity of the purified T-cells 4 groups of Balb/c mice were implanted with A20 cells (0.2 mL of 5×10⁶ cells s.c./mouse). One group received no treatment, the other three group were treated when the A20 cells reached 100 mm³ and were treated either with daily 20 mM 2FF in the drinking water, 2×10⁶ T-cells isolated from control tumor bearing mice injected IP, or 2×10⁶ T-cells isolated from 2FF tumor bearing mice injected IP. Animals were monitored for subsequent tumor progression. Animals who received either daily 2FF in their water or CD3⁺ T cells isolated from tumor bearing 2FF treated animals showed significantly delayed tumor growth and in some cases tumor regression when compared to untreated animals or those received T cells from untreated tumor bearing mice.

These data indicate that 2FF anti-tumor activity in the A20 lymphoma model is not only mediated through T cell responses, but T cells from tumor bearing mice treated with 2FF are surprisingly sufficient to drive an anti-tumor response and this response is on par with systemic 2FF treatment. These findings open up the possibility of using 2FF to amplify T cell activity in therapeutic situations where autologous T cells from cancer patients are expanded ex vivo and reinstalled in patients, or transformed with TCRs to specific tumor antigens, or CAR constructs.

Example 3—Ex-Vivo Expansion of Human Peripheral T Cells with 2FF for In Vivo Anti-Tumor Efficacy T cells were isolated from 10 mL of whole blood which was centrifuged first at 1200 rpm (300×g) for 10 min (without brakes). The top layer containing platelets was removed carefully without disrupting the white blood cell layer. Then RosetteSep™ Human T-Cell Enrichment Cocktail (Pan T Cells from StemCell technologies) was added to the remaining blood (500 μLAO mL blood). This was incubated for 20 min and then 1 mL FBS was added along with 10 mL PBS. Histopaque (20-25 mL) placed in a 50 mL Falcon the prepared blood/PBS solution was overlaid very slowly. This was centrifuged with no brake (25° C., 1500 rpm, 25 min). The top layer was removed and the T cells in the buffy coat layer were then removed to a new 50 mL tube. The T cells were washed with PBS, resuspended in 1 mL AKT lysis buffer and topped up to 25 mL, incubated for 5 min, brought up to 50 mL with PBS, and then pelleted. This red blood cell lysis step was repeated a second time.

Figure 4:
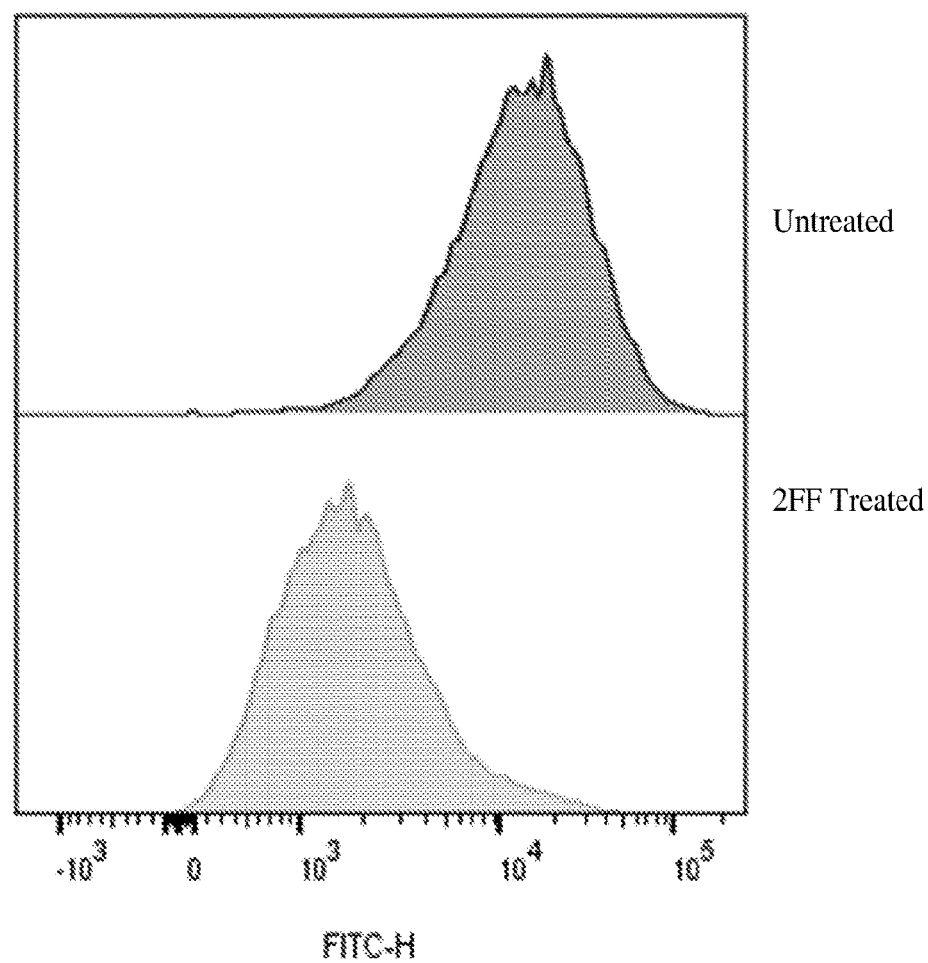
FIG. 4 shows a graph demonstrating reduced surface fucosylation of CD3+ T cells isolated from human donors following ex-vivo treatment with 100 mM 2FF as determined by surface LCA staining.

For in vitro culturing of primary human T cell culture, isolated T cells were re-suspended in T cell media (RPMI media supplemented with 10% Fetal calf serum (FCS), 1% Penicillin and moved into two T25 flasks, one with or and one without 100 μM 2-deoxy-2-fluoro-L-fucose. CD3/CD28 antibody coated beads (20 μL/flask) were added to activate the T cells. After 24 hr interleukin 2 (IL2) was added (100 ng/μL). Each time the cells were passaged new IL2 and 2-deoxy-2-fluoro-L-fucose were added. After 10 days in culture, expanded T cells cultured in 2FF were assessed for changes in surface fucosylation by flow cytometry (FIG. 4). Treatment of primary human T cells with 2FF results in about 85% decrease in surface fucosylation as monitored by lens culinaris agglutinin (LCA) surface staining and indicates that the cells are ready for in vivo transfer.

Example 4—Autologous T Cell Matured and Differentiated with 2FF Ex Vivo can Confer Anti-Tumor Activity Peripheral blood mononuclear cells were isolated from the buffy coats of venous blood from voluntary healthy volunteers (Astarte Biologics) using a histopaque (Sigma) density gradient. T cells were subsequently isolated using the EasySep Human T cell Enrichment Cocktail (STEMCELL) following the manufactures instructions. αCD3/αCD28 antibody coated beads (Miltenyi Biotec), used at a 1:8 bead:cell ratio, were used to activate the T cells on day 0. T cells were activated in RPMI 10% FCS+IL-2 (100 ng/μL, R&D Systems)+/−100 μM 2FF. Each time the cells were passaged new IL-2 and 2FF were added.

Epstein Ban virus (EBV) transformed lymphoblastoid cell lines (LCL) were implanted subcutaneously into NSG mice. When LCL tumor volumes reached 300 mm³, mice received 2.0×10⁶ autologous peripheral T cells, that were expanded and matured in the presence or absence of 2FF via tail vein injection. Anti-tumor activity of autologous T cells on LCL progression was monitored by bi-weekly caliper measurements. Mice were sacrificed once tumors sized out or receded completely for more than 1 week.

Figure 5A:
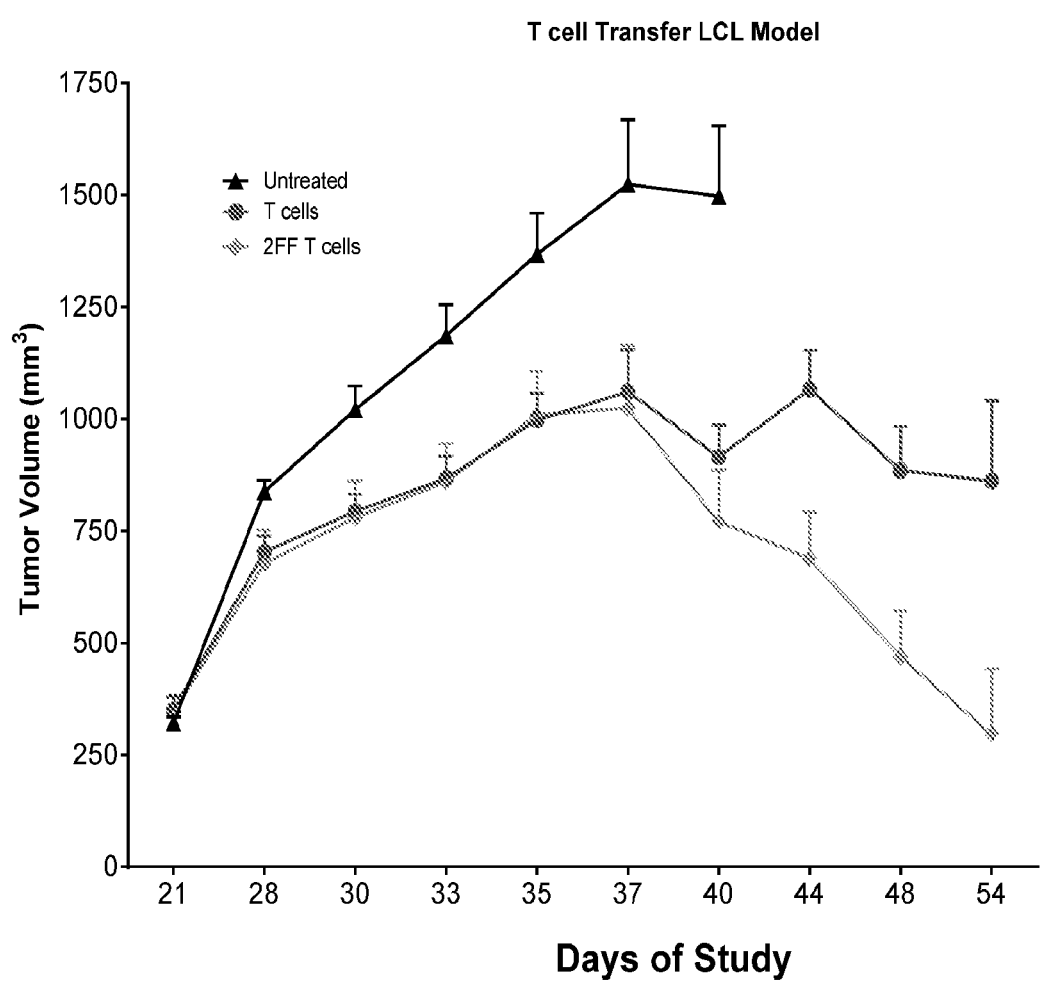
FIGS. 5A-5B show graphs demonstrating tumor progression after autologous human T cells matured in the presence or absence of 2FF were transferred into NSG mice bearing matched LCL EBV transformed B cell tumors.
Figure 5B:
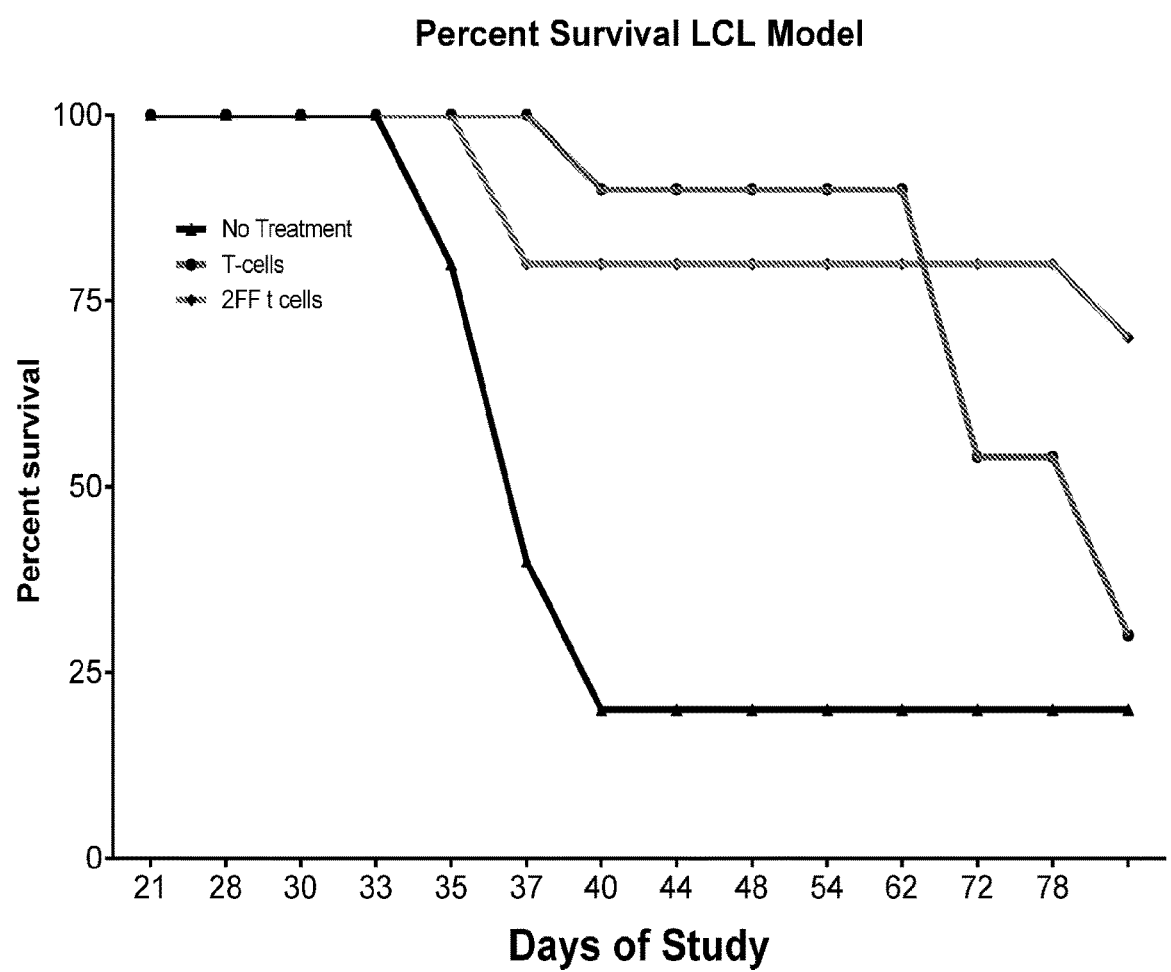

Transfer of autologous T cells resulted in anti-tumor activity, and this activity was significantly enhanced (see FIG. 5A) as was survival (see FIG. 5B) when T cells were matured with 2FF prior to transfer.

What is claimed is:

1. A method of producing T cells having reduced surface fucosylation, the method comprising:
    culturing T cells in the presence of an effective amount of a fucose analog in a cell culture medium; wherein said fucose analog is selected from the group consisting of formulae (I) and (II):

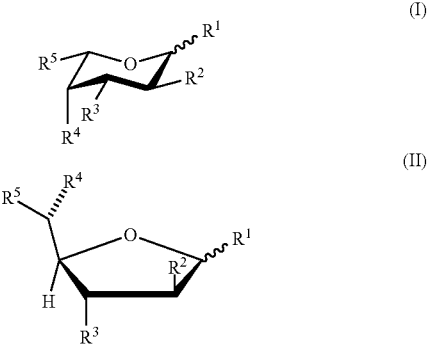

or a pharmaceutically acceptable salt or solvate form thereof, wherein each of formula (I) or (II) can be the alpha or beta anomer or the corresponding aldose form;
    $R^2$ is halogen; each of $R^1$, $R^3$, and $R^4$ is independently —OH or a hydrolyzable ester group; and $R^5$ is —CH₃, or
    each of $R^1$, $R^2$, $R^3$, and $R^4$ is independently —OH or a hydrolyzable ester group; and $R^5$ is —C≡CH;
    and
    wherein said T cells cultured in the presence of the effective amount of said fucose analog have at least about 80% reduced surface fucosylation relative to T cells cultured in the absence of said fucose analog; and wherein the T cells having reduced surface fucosylation are configured to be used in an adoptive cell therapy.

2. The method of claim 1, further comprising a step of isolating the T cells having reduced surface fucosylation.

3. The method of claim 1, wherein the fucose analog is 2-deoxy-2-fluoro-L-fucose.

4. The method of claim 1, wherein the fucose analog is alkynyl fucose peracetate.

5. The method of claim 1, wherein said T cells comprise human peripheral T cells.

6. The method of claim 1, wherein said T cells having reduced surface fucosylation are T cells having at least about 85% reduction of surface fucosylation relative to T cells cultured in the absence of said fucose analog.

7. The method of claim 1, wherein said T cells having reduced surface fucosylation are T cells having at least about 90% reduction of surface fucosylation relative to T cells cultured in the absence of said fucose analog.

8. The method of claim 1, wherein said T cells having reduced surface fucosylation are T cells having at least about 95% reduction of surface fucosylation relative to T cells cultured in the absence of said fucose analog.

* * * * *